United States Patent
Schings et al.

(10) Patent No.: US 12,274,437 B2
(45) Date of Patent: Apr. 15, 2025

(54) SURGICAL STAPLER CARTRIDGE WITH 3D PRINTABLE FEATURES

(71) Applicant: Cilag GmbH International, Zug (CH)

(72) Inventors: Brian D. Schings, Maineville, OH (US); Gregory J. Bakos, Mason, OH (US); Zhifan F. Huang, Mason, OH (US); Luke C. Ice, Garrett, IN (US); Sudhir Patel, Cincinnati, OH (US); Jason L Harris, Lebanon, OH (US); Pravin S. Pawar, Islampur (IN); Prabakaran Ravichandran, Mayiladuthurai (IN)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/951,602

(22) Filed: Sep. 23, 2022

(65) Prior Publication Data
US 2023/0309991 A1    Oct. 5, 2023

(30) Foreign Application Priority Data
Mar. 29, 2022    (IN) .............................. 202211018496

(51) Int. Cl.
*A61B 17/068*    (2006.01)
*A61B 17/072*    (2006.01)

(52) U.S. Cl.
CPC .. *A61B 17/068* (2013.01); *A61B 2017/07257* (2013.01)

(58) Field of Classification Search
CPC ................ A61B 17/072; A61B 17/068; A61B 2017/07271; A61B 2017/07278
See application file for complete search history.

(56) References Cited

U.S. PATENT DOCUMENTS 5,653,928 A * 8/1997 Schnipke ......... A61B 17/07207
264/249
5,820,009 A * 10/1998 Melling ........... A61B 17/07207
227/176.1

(Continued)

FOREIGN PATENT DOCUMENTS

| EP | 3120781 A2 | 1/2017 |
| EP | 3202337 A1 | 8/2017 |
| EP | 3730069 A1 | 10/2020 |

OTHER PUBLICATIONS

International Search Report and Written Opinion dated Jun. 15, 2023 for Application No. PCT/IB2023/053083, 15 pgs.

(Continued)

*Primary Examiner* — Gloria R Weeks
(74) *Attorney, Agent, or Firm* — Frost Brown Todd LLP

(57) ABSTRACT

An apparatus includes a staple, a body, a staple driver, and an alignment feature. The alignment feature is coupled to or formed with at least one of the staple driver or an inner surface of the staple aperture of the body. The alignment feature is configured to minimize rotation of the staple driver. The alignment feature includes at least one of a first contact feature, an alignment member, an alignment member, or an inwardly tapering portion. The first contact feature projects beyond a first lateral side of the staple driver. The alignment member extends through at least a portion of the staple driver. The first connecting portion rigidly connects the inner surface of the staple aperture with the staple driver in a connected state. The inwardly tapering portion of the inner surface or the staple driver is configured to guide the staple driver.

20 Claims, 21 Drawing Sheets

(56) References Cited

U.S. PATENT DOCUMENTS

| | | | |
|---|---|---|---|
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,800,838 B2 * | 8/2014 | Shelton, IV | A61B 17/07207 |
| | | | 227/176.1 |
| 9,131,940 B2 | 9/2015 | Huitema et al. | |
| 9,186,142 B2 | 11/2015 | Fanelli et al. | |
| 9,517,065 B2 * | 12/2016 | Simms | A61B 17/068 |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,801,628 B2 * | 10/2017 | Harris | A61B 17/072 |
| 9,808,248 B2 | 11/2017 | Hoffman | |
| 9,936,954 B2 * | 4/2018 | Shelton, IV | A61B 17/07292 |
| 10,092,292 B2 | 10/2018 | Boudreaux et al. | |
| 10,172,620 B2 * | 1/2019 | Harris | B32B 3/266 |
| 10,433,845 B2 * | 10/2019 | Baxter, III | A61L 31/148 |
| 10,548,597 B2 * | 2/2020 | Dunki-Jacobs | A61B 17/32 |
| 10,631,945 B2 * | 4/2020 | Eschbach | G01L 5/0061 |
| 10,709,452 B2 | 7/2020 | DiNardo et al. | |
| 10,792,042 B2 * | 10/2020 | Matonick | A61B 17/07292 |
| 10,939,911 B2 * | 3/2021 | Huitema | A61B 17/07292 |
| 10,952,724 B2 * | 3/2021 | Shelton, IV | A61B 17/0644 |
| 11,045,193 B2 | 6/2021 | Schings et al. | |
| 11,266,403 B2 | 3/2022 | Simms | |
| 11,432,815 B2 | 9/2022 | Courtwright et al. | |
| 11,596,291 B2 * | 3/2023 | Harris | A61B 17/1155 |
| 11,660,084 B2 * | 5/2023 | Khalil | A61B 17/068 |
| | | | 606/232 |
| 11,944,299 B2 * | 4/2024 | Shelton, IV | A61B 17/07207 |
| 2015/0297225 A1 * | 10/2015 | Huitema | A61B 17/105 |
| | | | 227/176.1 |
| 2018/0168625 A1 * | 6/2018 | Posada | A61B 17/07207 |
| 2020/0046356 A1 * | 2/2020 | Baxter, III | A61L 31/022 |
| 2021/0153861 A1 * | 5/2021 | Khalil | A61B 17/07292 |
| 2022/0304679 A1 * | 9/2022 | Bakos | B33Y 80/00 |
| 2022/0304681 A1 * | 9/2022 | Shelton, IV | A61B 17/0686 |
| 2022/0370065 A1 * | 11/2022 | Shelton, IV | A61B 17/072 |
| 2023/0051305 A1 | 2/2023 | Jones et al. | |
| 2023/0309996 A1 * | 10/2023 | Baxter, III | B33Y 80/00 |
| | | | 227/178.1 |

OTHER PUBLICATIONS

International Search Report and Written Opinion dated Sep. 8, 2023 for Application No. PCT/IB2023/053078, 18 pgs.

* cited by examiner

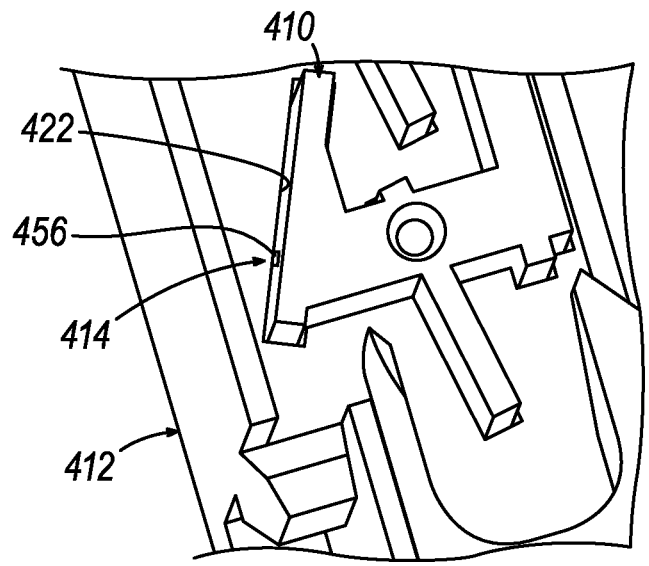
FIG. 19
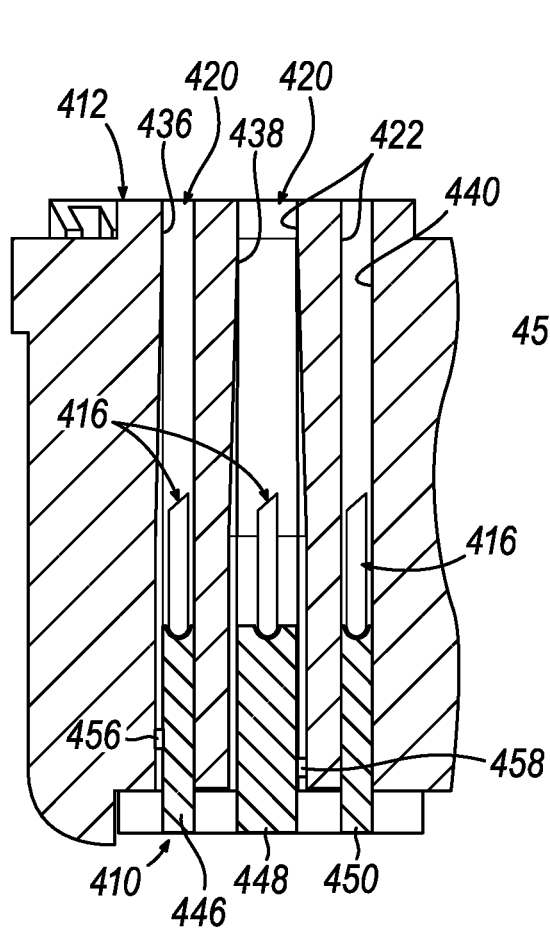 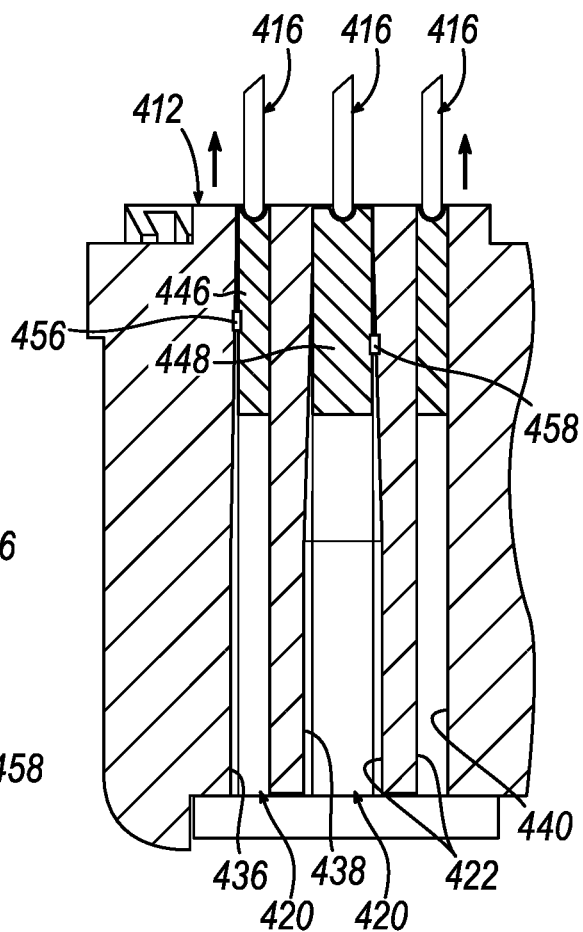
FIG. 20A  FIG. 20B

SURGICAL STAPLER CARTRIDGE WITH 3D PRINTABLE FEATURES

PRIORITY

This application claims priority to Indian Provisional Pat. App. No. 202211018496, entitled "Surgical Stapler Cartridge with 3D Printable Features," filed on Mar. 29, 2022.

BACKGROUND

Examples of surgical instruments include surgical staplers, which may be configured for use in laparoscopic surgical procedures and/or open surgical procedures. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein in its entirety.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 19 depicts a perspective view of the cartridge body and the staple drivers of FIG. 18;

FIG. 20A depicts a partial perspective view of the cartridge body and the staple driver of FIG. 18 in a non-actuated position;

FIG. 20B depicts a partial perspective view of the cartridge body and the staple driver of FIG. 20A, but after the staple driver has advanced staples through a deck surface of the cartridge body;

Figure 1:
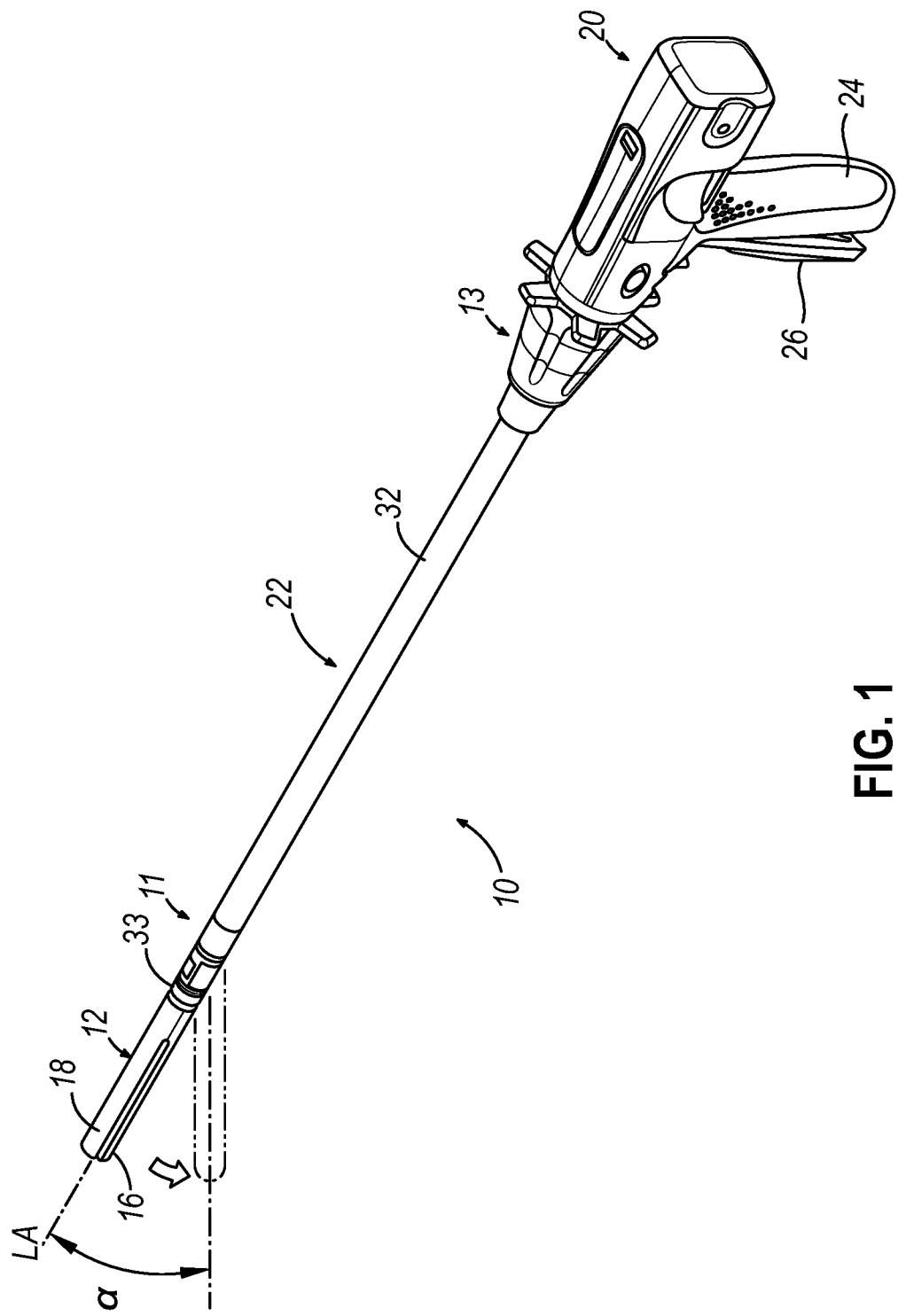
FIG. 1 depicts a perspective view of an example of an articulating surgical stapling instrument.
Figure 2:
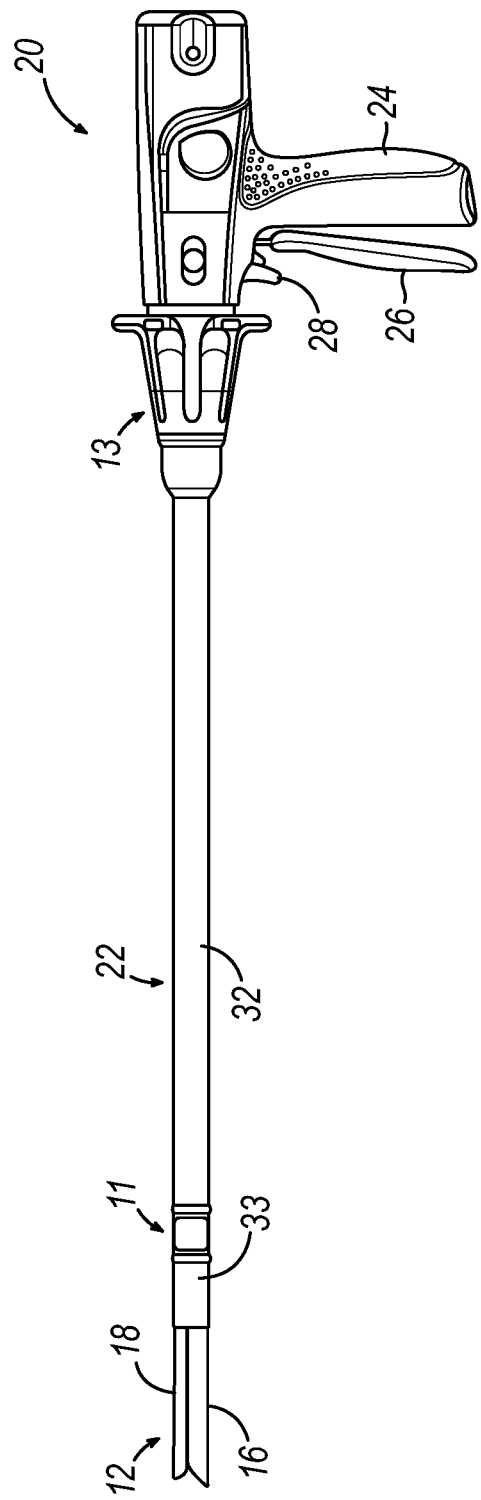
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. Exemplary Surgical Stapler

FIGS. 1-7 depict an example of a surgical stapling and severing instrument (10) that is sized for insertion, in a nonarticulated state as depicted in FIG. 1, through a trocar cannula, thoracotomy, or other incision to a surgical site in a patient for performing a surgical procedure. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20).

Once articulation joint (11) and end effector (12) are inserted into the patient, articulation joint (11) may be remotely articulated, as depicted in phantom in FIG. 1, by an articulation control (13), such that end effector (12) may be deflected from the longitudinal axis (LA) of shaft (22) at a desired angle (a). By way of example only, articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety; and/or U.S. Pat. No. 9,795,379, entitled "Surgical Instrument with Multi-Diameter Shaft," issued Oct. 24, 2017, the disclosure of which is incorporated by reference herein in its entirety. Other suitable forms that articulation joint (11) and articulation control (13) may take will be apparent to those skilled in the art in view of the teachings herein.

End effector (12) of the present example includes a lower jaw (16) and an upper jaw in the form of a pivotable anvil (18). By way of example only, lower jaw (16) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (18) may be constructed and operable in accordance with at least some of the teachings of at least some of the teachings of U.S. Pat. No. 10,092,292, entitled "Staple Forming Features for Surgical Stapling Instrument," issued Oct. 9, 2018, the disclosure of which is incorporated by reference herein in its entirety. Other suitable forms that lower jaw (16) and anvil (18) may take will be apparent to those skilled in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of tissue clamped in end effector (12), as will be described in greater detail below. Thereafter, triggers (26, 28) may be released to release the tissue from end effector (12).

Figure 4A:
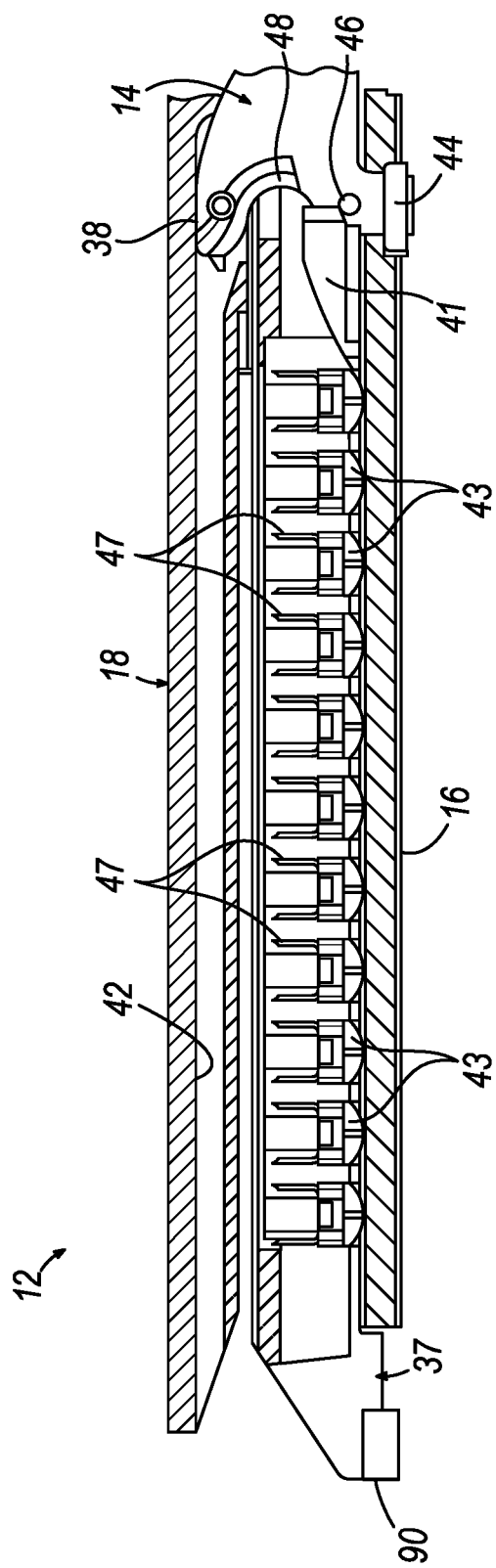
FIG. 4A depicts a side cross-sectional view of the end effector of FIG. 3, taken along line 4-4 of FIG. 3, with a firing beam in a proximal position.
Figure 4B:
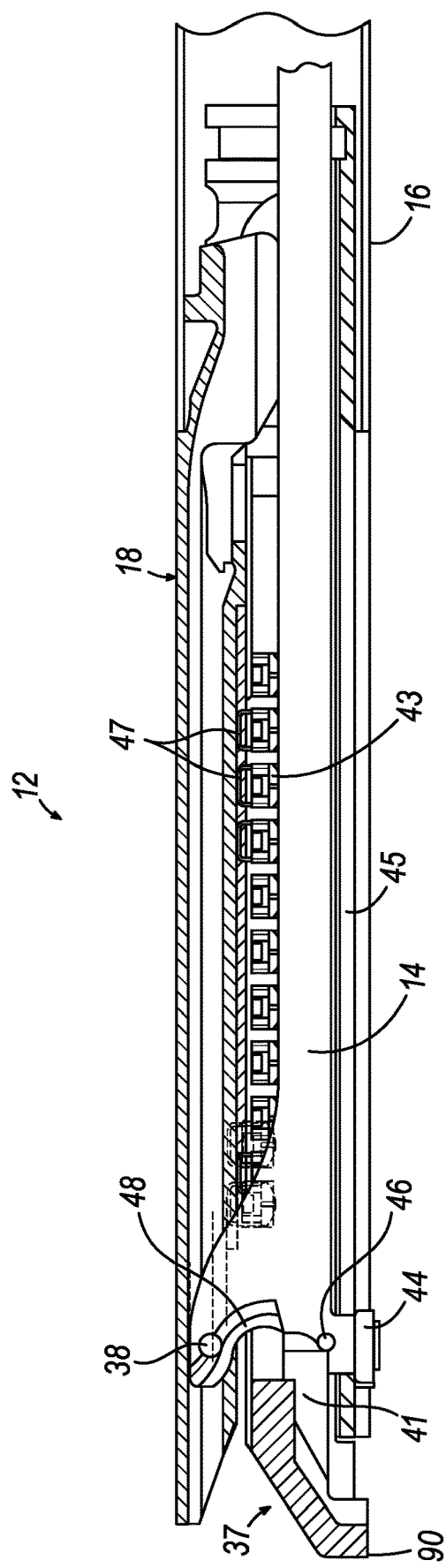
FIG. 4B depicts a side cross-sectional view of the end effector of FIG. 3, taken along line 4-4 of FIG. 3, with the firing beam in a distal position.

As best seen in FIGS. 4A-4B, firing beam (14) of the present example includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam

(14) affirmatively spaces end effector (12) during firing. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein in its entirety. Other suitable forms that firing beam (14) may take will be apparent to those skilled in the art in view of the teachings herein.

Figure 3:
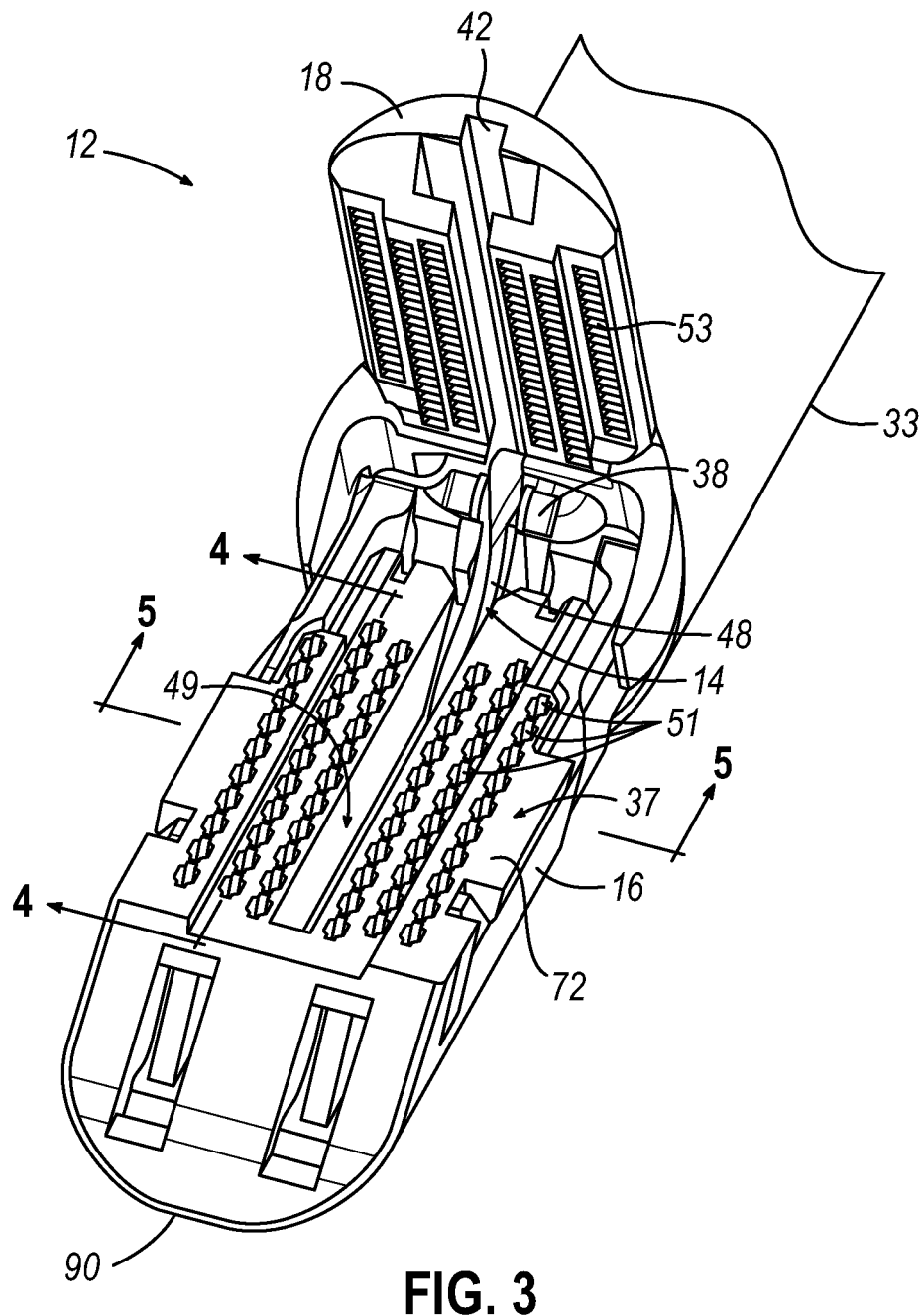
FIG. 3 depicts a perspective view of an opened end effector of the instrument of FIG. 1.
Figure 5:
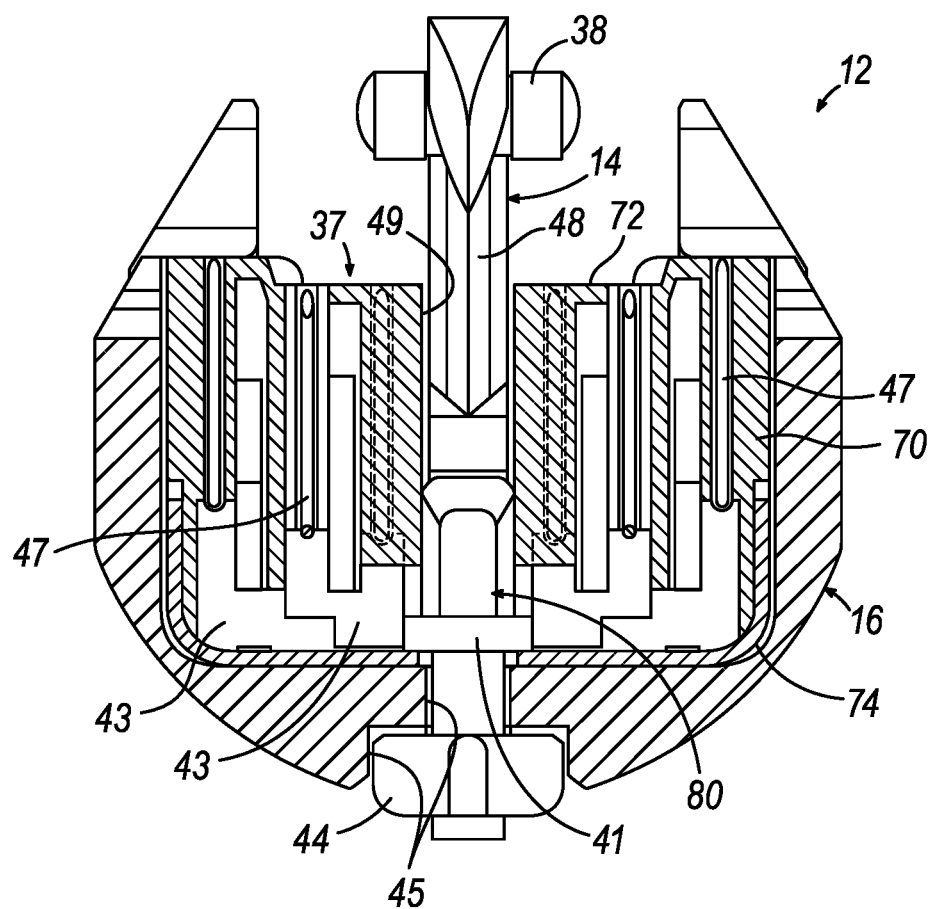
FIG. 5 depicts an end cross-sectional view of the end effector of FIG. 3, taken along line 5-5 of FIG. 3.
Figure 6:
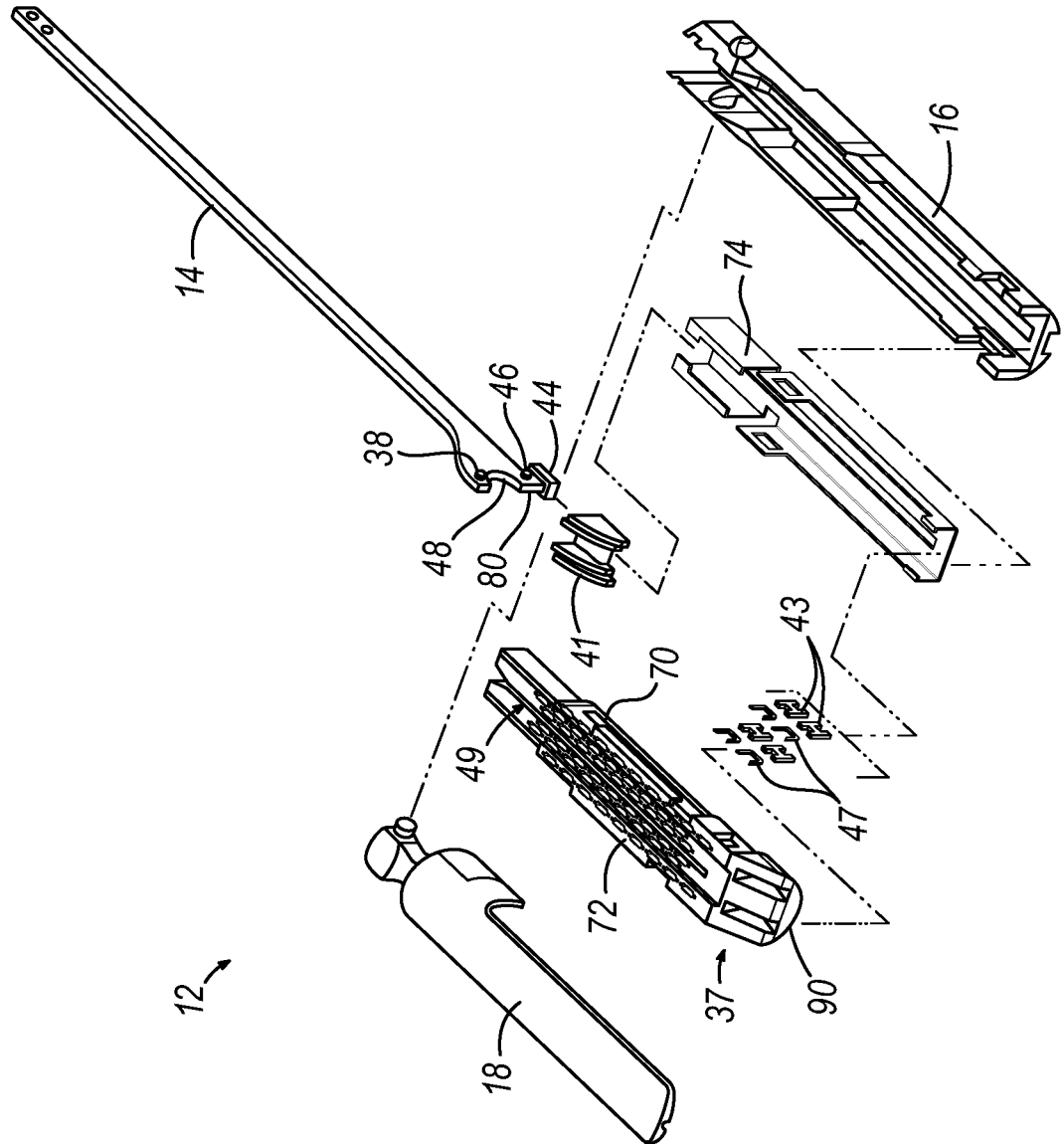
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a tray (74). Cartridge body (70) includes a distal end (90). As best seen in FIG. 3, a vertical slot (49) is formed through part of staple cartridge (37). Three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43) when staple cartridge (37) is in a pre-fired (or "unspent") state. Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

By way of example only, staple cartridge (37) may be constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein in its entirety. Other suitable forms that staple cartridge (37) may take will be apparent to those skilled in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) located at the distal end of firing beam (14) is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
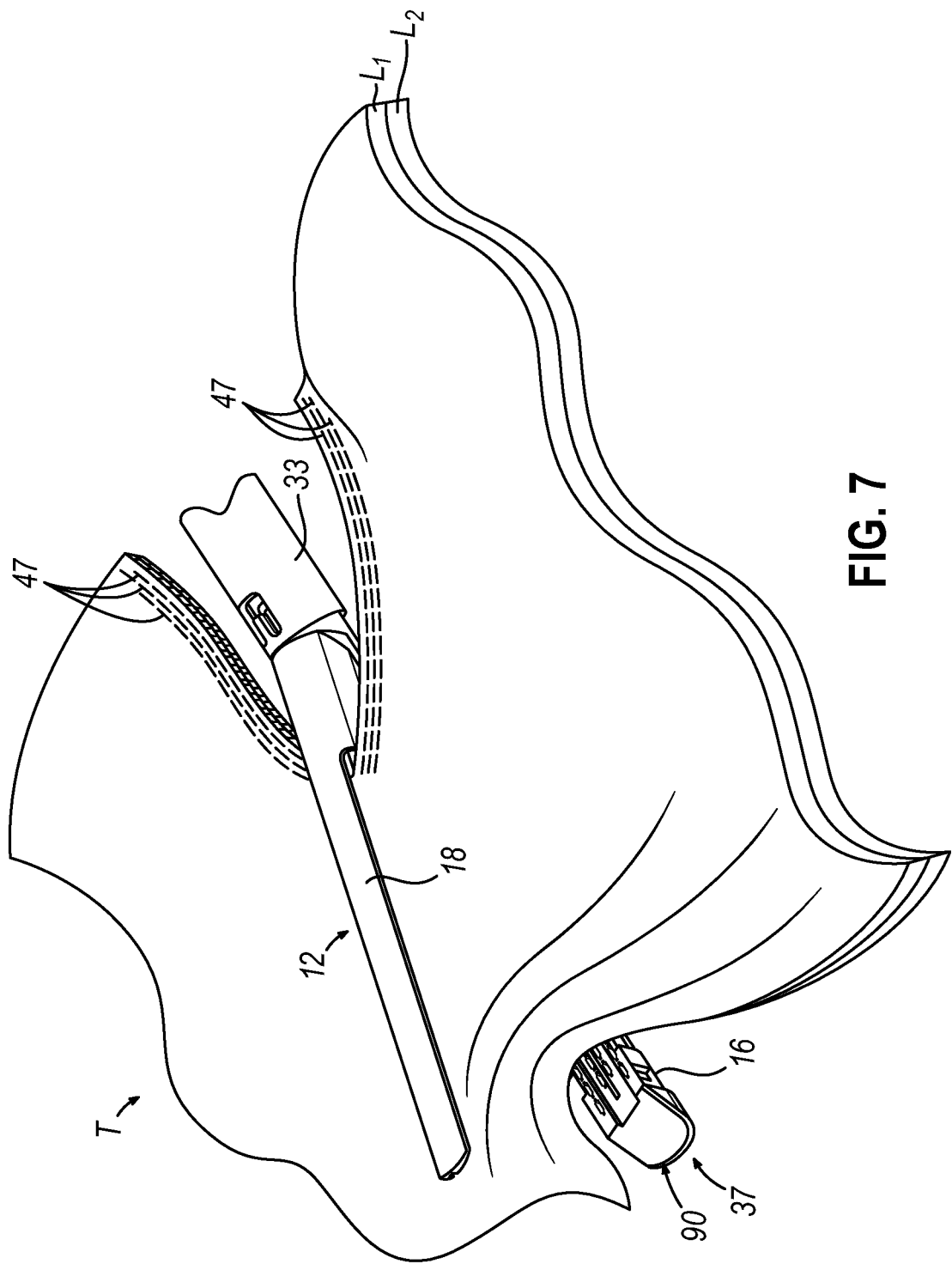
FIG. 7 depicts a perspective view of the end effector of FIG. 3, positioned at tissue and having been actuated once in the tissue.

FIG. 7 shows end effector (12) having been actuated through a single stroke through layers ($L_1$, $L_2$) of tissue (T). As shown, cutting edge (48) (obscured in FIG. 7) has cut through tissue (T), while staple drivers (43) have driven three alternating rows of staples (47) through the tissue (T) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar or incision after the first stroke is complete, spent staple cartridge (37) is replaced with a new staple cartridge, and end effector (12) is then again inserted through the trocar or incision to reach the stapling site for further cutting and stapling. This process may be repeated until the desired number of cuts and staples (47) have been provided. Anvil (18) may need to be closed to facilitate insertion and withdrawal through the trocar; and anvil (18) may need to be opened to facilitate replacement of staple cartridge (37).

In some versions, instrument (10) provides motorized control of firing beam (14). By way of example only, such motorization may be provided in accordance with at least some of the teachings of U.S. Pat. No. 9,622,746, entitled "Distal Tip Features for End Effector of Surgical Instrument," issued Apr. 18, 2017, the disclosure of which is incorporated by reference herein in its entirety; and/or U.S. Pat. No. 8,210,411, entitled "Motor-Driven Surgical Instrument," issued Jul. 3, 2012, the disclosure of which is incorporated by reference herein in its entirety. Other suitable components, features, and configurations for providing motorization of firing beam (14) will be apparent to those skilled in the art in view of the teachings herein. It should also be understood that some other versions may provide manual driving of firing beam (14), such that a motor may be omitted.

II. Exemplary Alignment Features

A. Overview

The manufacture and/or assembly of stapling assemblies (e.g., staple cartridges (37)) may be complicated, costly, and time consuming for a variety of reasons. These reasons include, for example, the number of components, the size of the components, the positioning of the components relative to one another within the stapling assembly, and the tight tolerances between components to ensure the desired functionality. For example, a precise fit between staple drivers (43) and staple apertures (51) of cartridge body (70) is desired to ensure accurate stapling. In some instances, too tight of a fit between staple drivers (43) and staple apertures (51) may lead to the breakage or incomplete stapling in some instances. Too loose of a fit may cause staple drivers (43) to rotate or pivot with staple apertures (51), which may lead to the breakage or incomplete stapling in some instances.

These problems may be magnified when producing a single stapling assembly or a few stapling assemblies for testing purposes prior to mass production of stapling assemblies. While some portions of a prototype staple cartridge may be manufactured using injection molding, there are many tiny components that are desirably held in alignment relative to one another to obtain a functional staple cartridge (e.g., staple cartridge (37)). For at least these reasons, the product development cycle may be lengthy and prevent on the fly modifications. As a result, new iterations of stapling assemblies take a longer time to produce than desired. For example, it may take over six months of lead time to produce a reliable and accurate prototype of a stapling assembly even after the CAD is finalized. Ultimately, this may extend the project timeline significantly. As a result, it is desirable to rapidly produce stapling assemblies to shorten the product launch timeline, including producing stapling assemblies for prototyping, testing, and evaluation.

FIGS. 8-25 show exemplary staple drivers (110, 210, 310, 410, 510, 610, 710), exemplary cartridge bodies (112, 212, 312, 412, 512, 612, 712), exemplary alignment features (114, 214, 314, 414, 514, 614, 714), and exemplary staples (116a-b, 216, 316a-c, 416, 516, 616, 716) that may form a portion of a stapling assembly. It is envisioned that stapling assemblies include staple cartridges (e.g., staple cartridge (37)) as well as non-cartridge versions. As described above, staple cartridge (37) is configured to be operatively coupled with a staple cartridge receiving portion (e.g., lower jaw (16) of end effector (12)) of a surgical instrument (e.g., instrument (10)). Staple drivers (110, 210, 310, 410, 510, 610, 710) are similar to staple drivers (43) with differences described below. Cartridge bodies (112, 212, 312, 412, 512, 612, 712) are similar to cartridge body (70) with differences described below. Staples (116a-b, 216, 316a-c, 416, 516, 616, 716) are similar to staples (47) with differences described below.

As will be described below with reference to FIGS. 8-25, alignment features (114, 214, 314, 414, 514, 614, 714) are formed with coupled to at least one of staple driver (110, 210, 310, 410, 510, 610, 710) or cartridge body (112, 212, 312, 412, 512, 612, 712). For example, alignment features (114, 214, 314, 414, 514, 614, 714) may be integrally formed as a unitary piece together with staple driver (110, 210, 310, 410, 510, 610, 710) and/or cartridge body (112, 212, 312, 412, 512, 612, 712). In some versions, alignment feature (114, 214, 314, 414, 514, 614, 714) may be integrally formed as a unitary piece together with staple driver (110, 210, 310, 410, 510, 610, 710) and/or cartridge body (112, 212, 312, 412, 512, 612, 712) using at least one additive manufacturing process, which may include 3D printing. Use of 3D printing (e.g., instead of injection molding) may speed up the overall production of the stapling assembly (e.g., staple cartridge) while maintaining the desired fit between components. Alignment features (114, 214, 314, 414, 514, 614, 714) ensure a desired fit is maintained between staple driver (110, 210, 310, 410, 510, 610, 710) and cartridge body (112, 212, 312, 412, 512, 612, 712). While alignment features (114, 214, 314, 414, 514, 614, 714) described herein are described with respect to the manufacture and assembly of prototypes for testing new stapling assemblies, these principles also apply to the manufacture and assembly of stapling assemblies (e.g., staple cartridge (37)) manufactured for mass production.

As will be described in greater detail below with reference to FIGS. 8-25, cartridge bodies (112, 212, 312, 412, 512, 612, 712) include respective deck surfaces (118, 218, 318, 418, 518, 618, 718). Deck surfaces (118, 218, 318, 418, 518, 618, 718) include staple apertures (120a-b, 220, 320, 420, 520, 620, 720). Alignment features (114, 214, 314, 414, 514, 614, 714) are formed with to coupled to at least one of staple driver (110, 210, 310, 410, 510, 610, 710) or staple aperture (120a-b, 220, 320, 420, 520, 620, 720). Alignment features (114, 214, 314, 414, 514, 614, 714) are configured to minimize rotation of staple driver (110, 210, 310, 410, 510, 610, 710) as staple driver (110, 210, 310, 410, 510, 610, 710) advances staple (116, 216, 316, 416, 516, 616, 716) from a non-deployed state when through staple aperture (120a-b, 220, 320, 420, 520, 620, 720) of deck surface (118, 218, 318, 418, 518, 618, 718) to a deployed state through staple aperture (120a-b, 220, 320, 420, 520, 620, 720) of deck surface (118, 218, 318, 418, 518, 618, 718).

The teachings of this application may be applied to stapling assemblies of various types of surgical staplers, including endocutters, linear surgical staplers, right angle surgical staplers, and curved surgical staplers, for example. For example, the teachings of this application may be combined with various exemplary linear surgical staplers, such that those shown and described in U.S. Pat. No. 11,045,193, entitled "Anvil Assembly for Linear Surgical Stapler," issued Jun. 29, 2021, the disclosure of which is incorporated by reference herein in its entirety. The teachings of this application may be combined with various exemplary circular surgical staplers, such that those shown and described in U.S. Pat. No. 10,709,452, entitled "Methods and Systems for Performing Circular Stapling," issued Jul. 14, 2020, the disclosure of which is incorporated by reference herein in its entirety. The teachings of this application may be combined with various exemplary right angle surgical staplers, such that those shown and described in U.S. Pat. No. 11,266,403, entitled "Tissue Cutting Washer for Right Angle Surgical Stapler," issued Mar. 9, 2022, the disclosure of which is incorporated by reference herein in its entirety. The teachings of this application may be combined with various exemplary curved surgical staplers, such that those shown and described in U.S. Pub. No. 2022/0031317, entitled "Features to Enhance Staple Height Consistency in Curved Surgical Stapler," published Feb. 3, 2022, the disclosure of which is incorporated by reference herein in its entirety.

Figure 8:
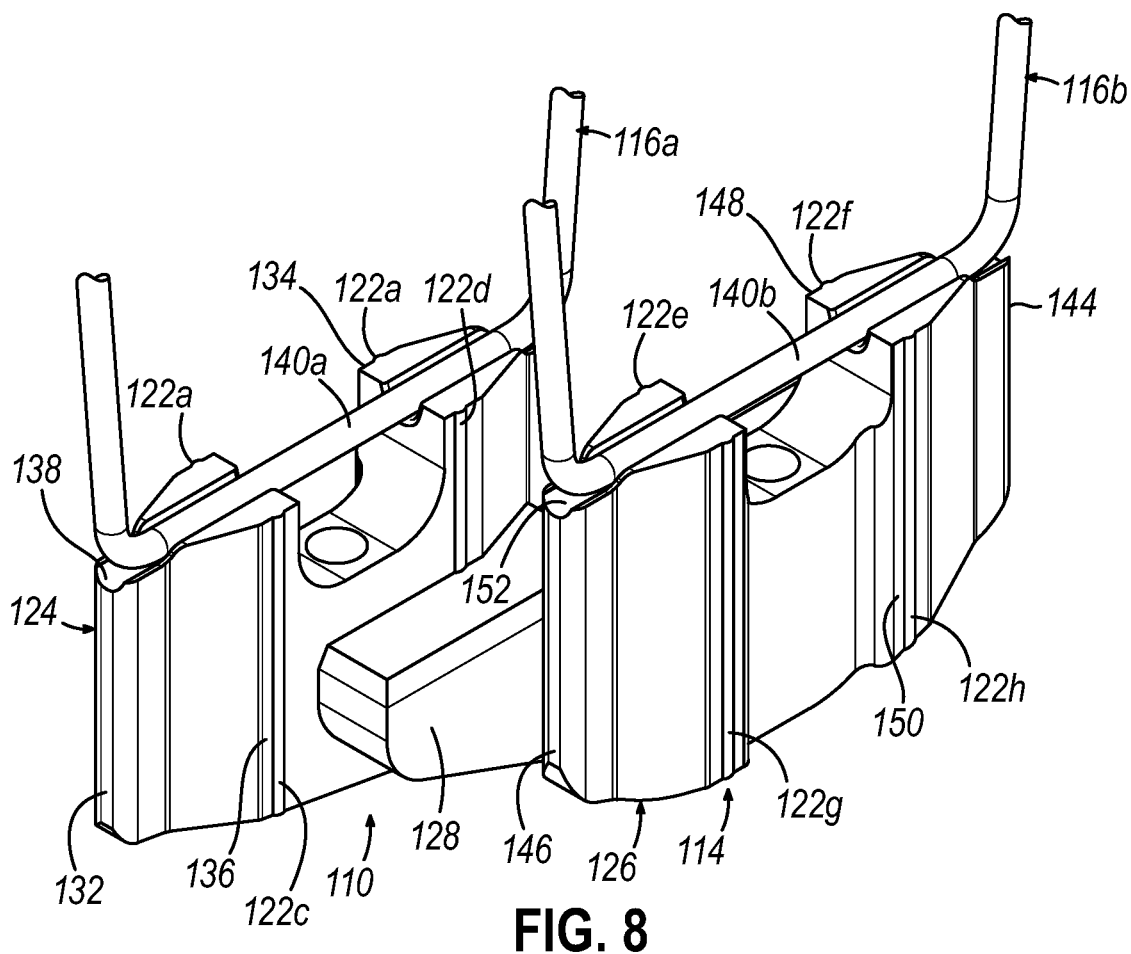
FIG. 8 depicts a perspective view of a first exemplary alternative staple driver that includes a first exemplary alignment feature and staples.
Figure 9:
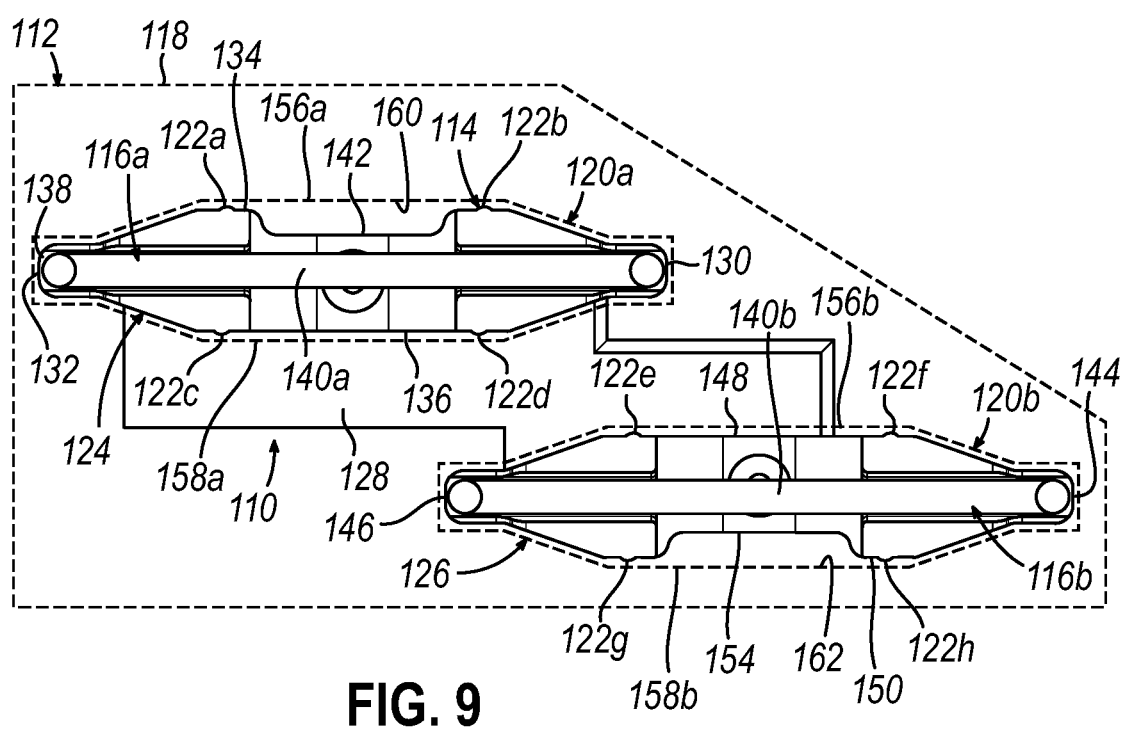
FIG. 9 depicts a top plan view of the staple driver and the staples of FIG. 8 with staple apertures of a first exemplary alternative cartridge body shown schematically in dashed lines.

B. First Exemplary Alternative Cartridge Body, First Exemplary Alternative Staple Driver, and First Exemplary Alignment Feature FIGS. 8-9 show a first exemplary alternative staple driver (110), a first exemplary alternative cartridge body (112), and a first exemplary alignment feature (114). As shown in FIG. 8, staple driver (110) includes first and second driver portions (124, 126) that are connected together using a linking portion (128). First driver portion (124) includes proximal and distal ends (130, 132) that are separated by first and second lateral sides (134, 136). First driver portion (124) includes a staple recess (138) configured to contact a crown (140a) of staple (116a) through staple aperture (120a). Second lateral side (136) is disposed opposite to first lateral side (134). First and second lateral sides (134, 136) may extend parallel to and offset from crown (140a) of staple (116a). As shown, first driver portion (124) includes an outer U-shaped cavity (142).

As shown in FIGS. 8-9, second driver portion (126) is a mirror image of first driver portion (124). Similar to first driver portion (124), second driver portion (126) includes proximal and distal ends (144, 146) that are separated by first and second lateral sides (148, 150). Second driver portion (126) includes a staple recess (152) configured to contact a crown (140b) of staple (116b) as staple (116b) moves within and through staple aperture (120a). Second lateral side (150) is disposed opposite to first lateral side (148). First and second lateral sides (148, 150) extend parallel to and offset from crown (140b) of staple (116b). As best shown in FIG. 9, second driver portion (126) includes an outer U-shaped cavity (154) that is disposed opposite to outer U-shaped cavity (154).

With continued reference to FIGS. 8-9, staple driver (110) includes alignment feature (114). Particularly, alignment feature (114) includes at least one contact feature (shown as contact features (122a-h)). Regarding first driver portion (124), first lateral side (134) includes contact features (122a-b), and second lateral side (136) includes contact features (122c-d). Regarding second driver portion (126), first lateral side (148) includes contact features (122e-f), and second lateral side (150) includes contact features (122g-h). More or fewer contact features (122a-h) are envisioned. For example, some of first and second lateral sides (134, 136, 148, 150) may not include contact features (122a-h), while other of first and second lateral sides (134, 136, 148, 150) may include more or fewer contact features (122a-h). Contact features (122a-h) are shown are oversized elongate lateral ribs that extend vertically. In some versions, contact features (122a-h) may be press fit onto staple drivers (110). In other versions, contact features (122a-h) may be integrally formed as a unitary piece together with staple driver (110) (e.g., using the same material as the remainder of staple driver (110)). For example, contact features (122a-h) may be 3D printed directly onto staple drivers (110) as staple drivers (110) are being formed. Using 3D printing allows for early evaluation of competing versions.

FIG. 9 schematically shows staple apertures (120a-b) of cartridge body (112) in dashed lines extends along a longitudinal axis (LA). Deck surface (118). Deck surface (118) includes staple apertures (120a-b). Staple aperture (120a) includes opposing first and second inner lateral walls (156a, 158a) that at least partially define an inner surface (160). Similarly, staple aperture (120b) includes opposing first and second inner lateral walls (156b, 158b) that at least partially define an inner surface (162). Staple driver (110) is configured to move within staple aperture (120a-b). As shown in FIG. 9, contact features (122a-b) are configured to contact first inner lateral wall (156a) of staple aperture (120a), and contact features (122c-d) are configured to contact second inner lateral wall (158a) of staple aperture (120a). Similarly, contact features (122e-f) are configured to contact first inner lateral wall (156b) of staple aperture (120b), and contact features (122g-h) are configured to contact second inner lateral wall (158b) of staple aperture (120b).

In some versions, at least one of contact features (122a-h) is formed from a compressible material that is more compressible than the remainder of staple driver (110). Forming contact features (122a-h) from a compressible material may allow for deformation of contact features (122a-h) to maintain a tight fit between staple driver (110) and staple apertures (120a-b) during travel of staple driver (110). In some versions, the tight fit allows for interference. For example, at least one of first and second inner lateral wall (156a, 158a) of staple aperture (120a) may deform to accommodate the interference yet allow first driver portion (124) of staple driver (110) to move without breakage. Similarly, at least one of first and second inner lateral wall (156b, 158b) of staple aperture (120b) may deform to accommodate the interference and yet allow second driver portion (126) of staple driver (110) to move without breakage.

Contact features (122a-h) are configured to reduce rotation of staple driver (110) as staple driver (110) advances staples (116a-b) from a non-deployed state to a deployed state. In the non-deployed state, staples (116a-b) are positioned within staple apertures (120a-b). In the deployed state, staples (116a-b) are advanced within staple apertures (120a-b) and subsequently through deck surface (118). Contact features (122a-d) are configured to slidably contact inner surface (160) of staple aperture (120a), and contact features (122e-h) are configured to slidably contact inner surface (162) of staple aperture (120b). At least some of contact features (122a-h) may be in constant contact with inner surface (160, 162). Alternatively, contact features (122a-h) may be in intermittent contact with inner surface (160, 162). Contact features (122a-h) are configured to alter the fit between cartridge body (112) and staple driver (110) to avoid overly tight or loose arrangements.

While contact features (122a-h) are shown as being formed with staple driver (110), it is also envisioned that contact features (122a-h) may be formed with staple aperture (120a-b). Particularly, it is also envisioned that at least one of first and second inner lateral walls (156a-b, 158a-b) of staple apertures (120a-b) may include a contact feature (not shown) configured to interact with staple driver (110). In some versions, linking portion (128) may be omitted such that first and second driver portions (124, 126) may move independently from one another. It is envisioned that this may apply to single staple drivers pushing a single staple through a single aperture (similar to staple driver (43) pushing staple (47) through apertures (51)) as well a staple driver (110) pushing multiple staples (116a-b) through multiple staple apertures (120a-b).

C. Second Exemplary Alternative Cartridge Body, Second Exemplary Alternative Staple Driver, and Second Exemplary Alignment Feature After staple driver (43) is loaded, staple driver (43) may become displaced during subsequent loading of other staple drivers (43). For example, in some instances, the initially placed staple driver (43) may be partially or completely ejected from staple aperture (51). Additionally, tray (74) may be difficult to manufacture for prototyping purposes. As a result, it is desirable to retain staple drivers (43) in place within staple apertures (51) without using tray (74).

Figure 10:
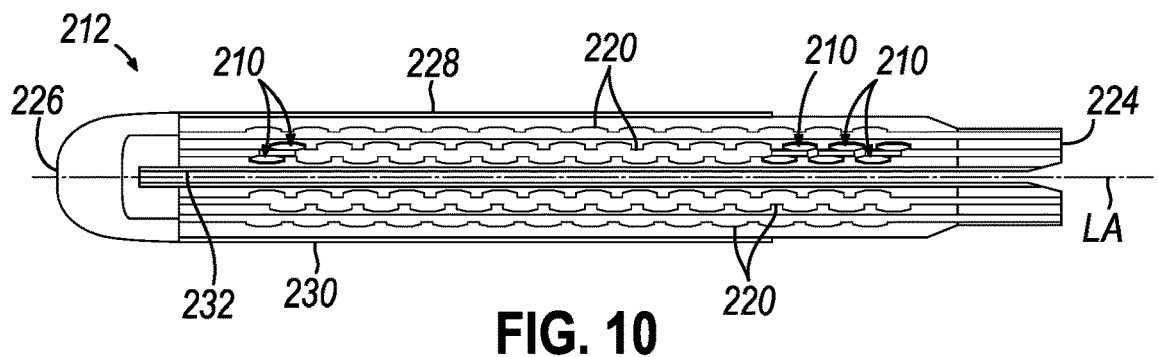
FIG. 10 depicts a bottom perspective view of a second exemplary alternative cartridge body and a second exemplary alternative staple driver.
Figure 11:
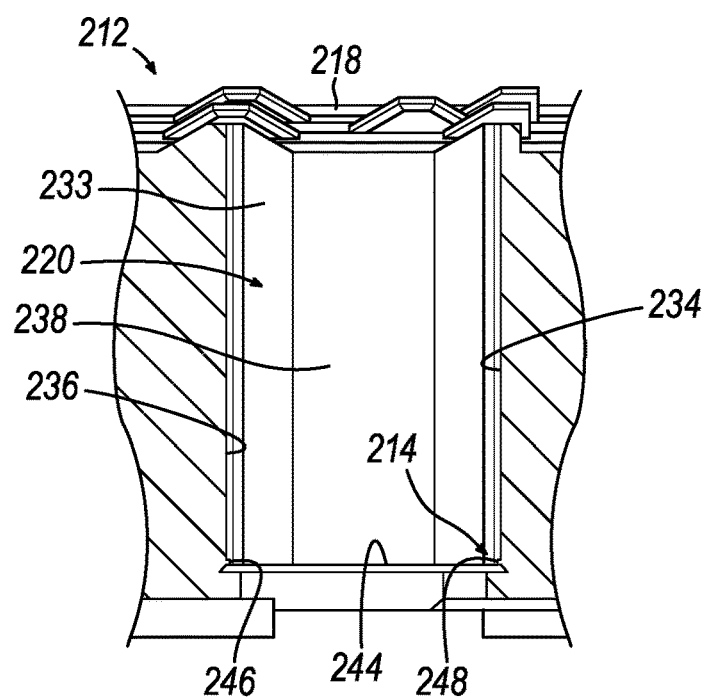
FIG. 11 depicts a partial perspective view of the cartridge body of FIG. 10, wherein the cartridge body includes a second exemplary alignment feature.
Figure 12:
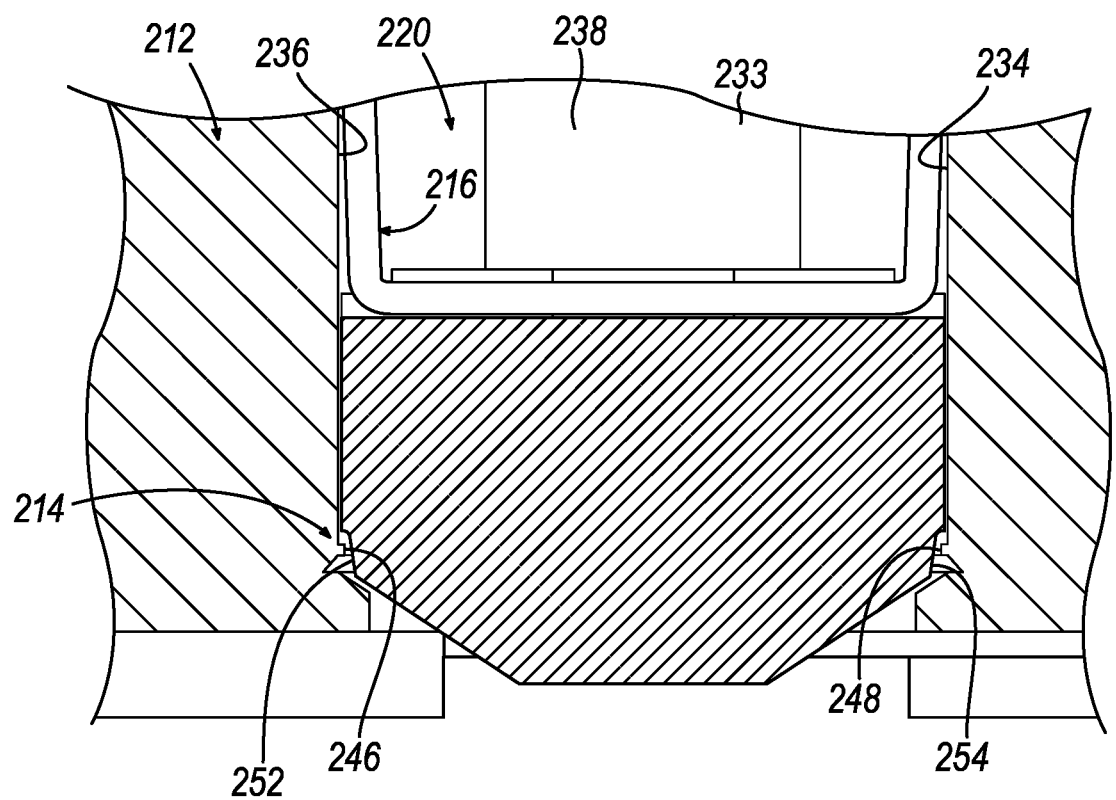
FIG. 12 depicts an enlarged perspective view of the staple driver disposed within cartridge body of FIG. 10 using the alignment feature.

FIGS. 10-12 show second exemplary alternative staple drivers (210), a second exemplary alternative cartridge body (212), and a second exemplary alignment feature (214). Cartridge body (212) extends along a longitudinal axis (LA). Cartridge body (212) includes a deck surface (218). Deck surface (218) includes a plurality of staple apertures (220). Cartridge body (212) includes a proximal end (224), a distal end (226), a first lateral side (228), and a second lateral side (230) disposed opposite to first lateral side (228). Cartridge body (212) also includes a knife slot (232) extending along longitudinal axis (LA). Staple aperture (220) is defined by an inner surface (233). Staple aperture (220) includes a proximal inner wall (234), a distal inner wall (236), a first inner lateral wall (238), and a second inner lateral wall (not shown). Staple aperture (220) also includes a lower surface (242) that may form a partial ledge to restrict movement of staple driver (210) from traveling to a bottom surface (244) of cartridge body (212).

Figure 11A:
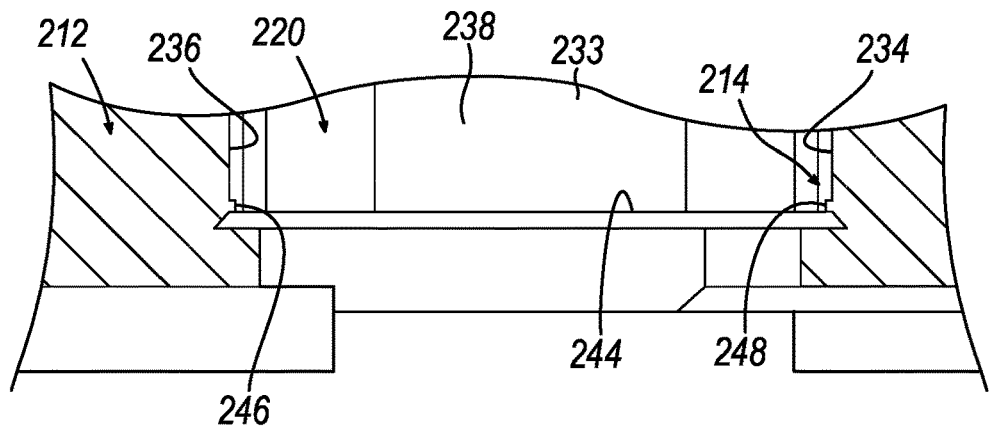
FIG. 11A depicts an enlarged perspective view of the alignment feature of the cartridge body of FIG. 11.

FIG. 11 shows a partial perspective view of cartridge body (212) of FIG. 10, where cartridge body (212) includes alignment feature (214) in the form of first and second tabs (246, 248), and FIG. 11A shows an enlarged perspective view of first and second tabs (246, 248). More or fewer tabs than first and second tabs (246, 248) are envisioned. Additionally, while alignment feature (214) is shown as first and second tabs (246, 248), a variety of other suitable alignment features (214) that retain staple driver (210) in the desired position are also envisioned. As shown, first and second tabs (246, 248) of alignment feature (214) are integrally formed as a unitary piece together with inner surface (233) of staple aperture (220). First and second tabs (246, 248) of alignment feature (214) may be located along proximal inner wall (234), and distal inner wall (236), first inner lateral wall (238), and second inner lateral wall (not shown), or any combination thereof. In some versions, first and second tabs (246, 248) may be flexible so as to allow the user to push staple driver (210) into staple aperture (220) without high force, yet be strong enough to sufficiently maintain staple (216) drive in position. Staple driver (210) may be press-fit during loading, so as to secure staple driver (210 against first and second tabs (246, 248). As a result, staple driver (210) is held in position during loading of staple drivers (210), handling, loading of staples, and during use. As staple driver (210) is pushed upward using a sled (e.g., wedge sled (41)) during instrument firing, the interference provided by first and second tabs (246, 248) is removed and the stapling or force required to eject the staples from the instrument (e.g., instrument 10)) is not affected.

FIG. 12 shows an enlarged perspective view of staple driver (210) retained within cartridge body (212) of FIG. 10 using first and second tabs (246, 248). First and second tabs (246, 248) may be 3D printed to allow staple drivers (210) to be securably held against cartridge body (212). Producing components using additive manufacturing may not result in the same manufacturing limitations as other manufacturing processes. For example, as shown in FIGS. 11-11A, 3D printing components (e.g., cartridge body (212)) does not require draft angles that used in injection molding processes to ensure the molded component sufficiently release from the mold cavity. Staple drivers (210) being self-retained within staple aperture (220) may provide for easier loading and handling of staples (216). Additionally, tray (74) may be omitted since stapler drivers (210) are self-retained within staple aperture (220) and prevented from moving toward bottom surface (244) using first and second tabs (246, 248). The removal of tray (74) may allow for cartridge body (212) to include additional material in the space previously occupied by tray (74). For example, the removal of tray (74) may allow for portions of cartridge body (212) to have thicker walls to increase the rigidity of cartridge body (212). In some versions, first and second tabs (246, 248) may be severed prior to shipping such that the tray (similar to tray (74)) be incorporated to retain staple drivers (210).

First and second tabs (246, 248) may align staple drivers (210) at a consistent height. This may prevent tips of staple (216) from protruding above deck surface (218) and/or provide improve the timing when staple drivers (210) are raised to deck surface (218) by sled (e.g., wedge sled (41)). Staple (216) may be positioned at the same height without any portion being extending outside of deck surface (218) of cartridge body (212) to prevent tissue trauma. Additionally, staple driver (210) does not travel too deep within staple aperture (220) so as to impact the performance of staple driver (210). In some versions, partial breakage or complete breakage of first and second tabs (246, 248) does not affect the function of staple driver (210) and cartridge body (212). Staple driver (210) remains held in position. Staple driver (210) may include first and second recesses (252, 254) improve the temporary binding of staple driver (210) within staple aperture (220). First and second recesses (252, 254) may respectively interact with first and second tabs (246, 248). First and second recesses (252, 254) may be initially formed within staple driver (210) or material from staple driver (210) may be removed during subsequent processing.

Figure 13:
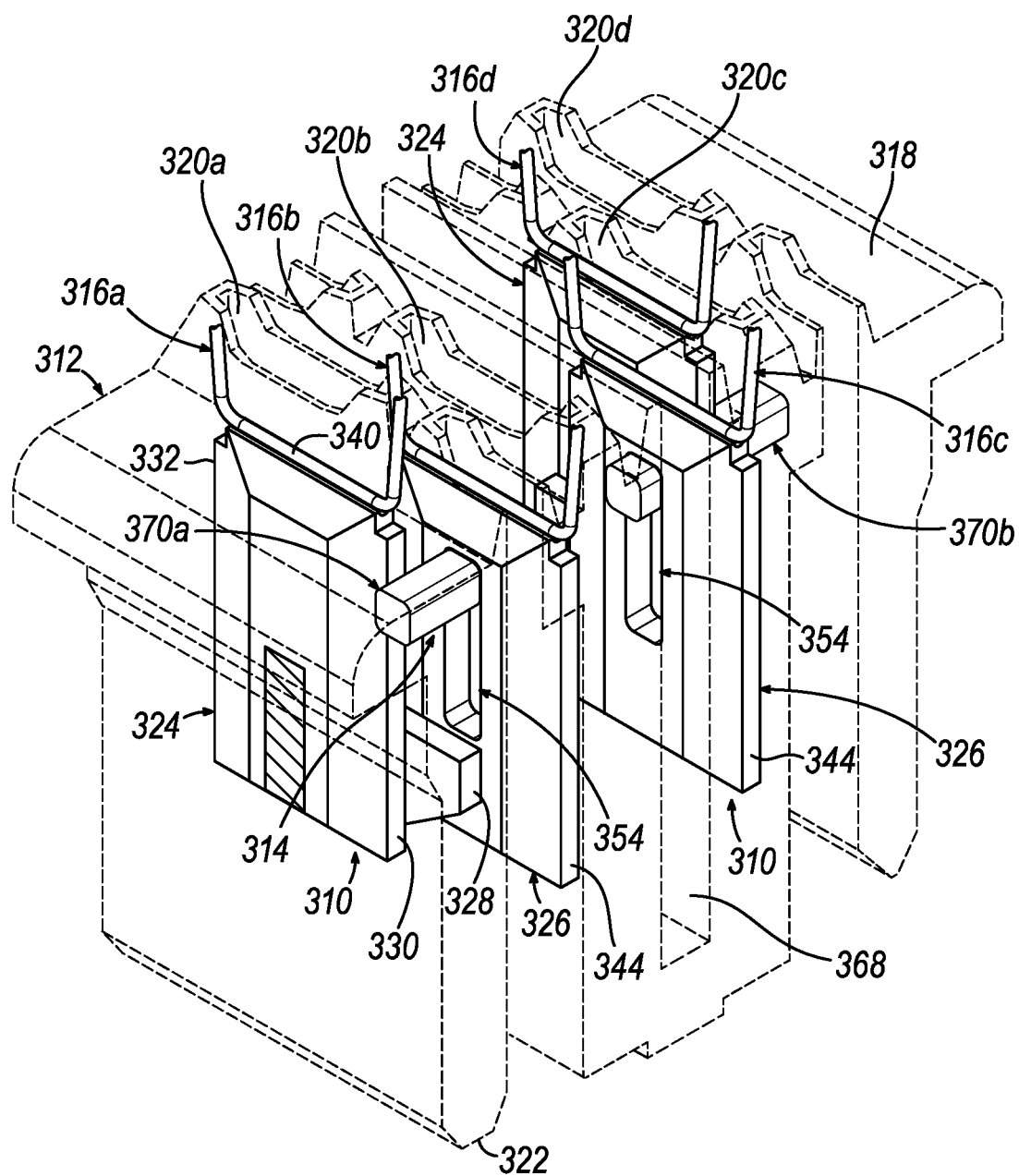
FIG. 13 depicts a perspective view of a portion of a third exemplary alternative cartridge body, and a third exemplary alternative staple driver.
Figure 15:
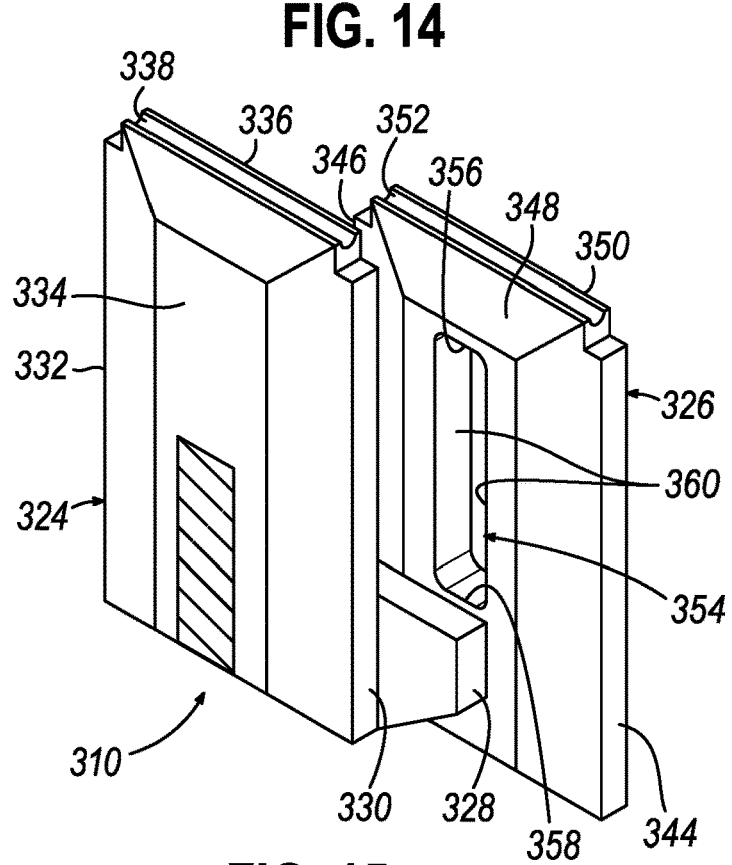
FIG. 15 depicts a perspective view of the staple driver of FIG. 13 configured to receive the alignment feature of FIG. 14.
Figure 16A:
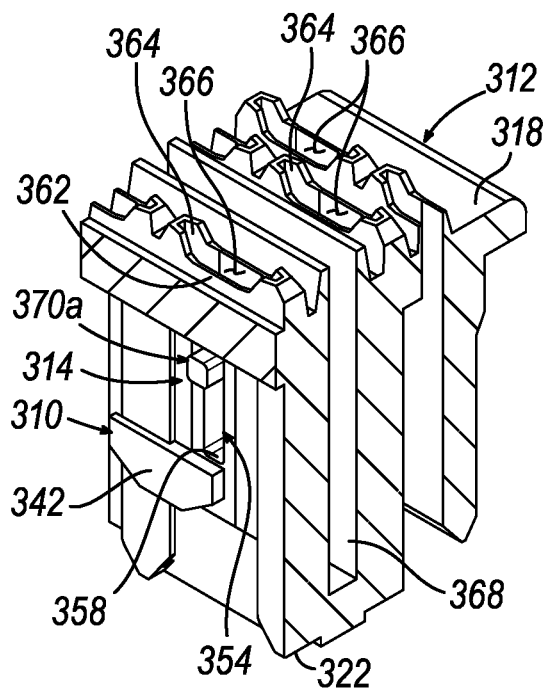
FIG. 16A depicts a partial perspective view of the cartridge body and the staple driver of FIG. 13 in a non-actuated position.
Figure 16B:
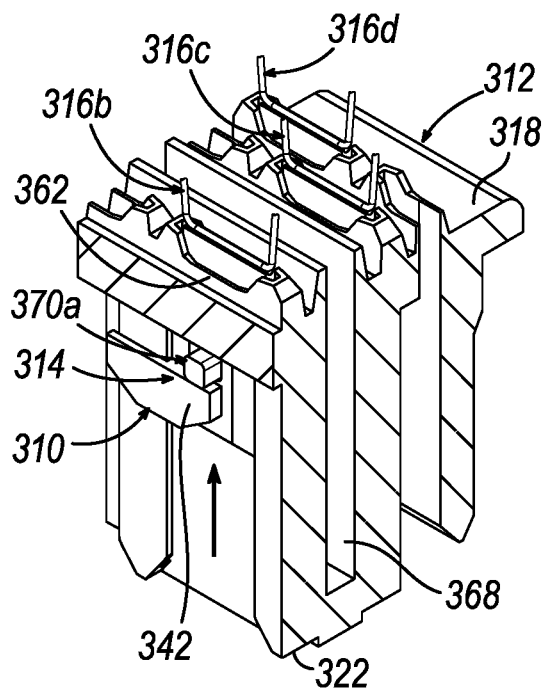
FIG. 16B depicts a partial perspective view of the cartridge body and the staple driver of FIG. 16A, but after the staple driver has advanced staples through a deck surface of the cartridge body.

D. Third Exemplary Alternative Staple Drivers, Third Exemplary Alternative Cartridge Body, and Third Exemplary Alignment Features FIG. 13 shows a perspective view of third exemplary alternative staple drivers (310) interacting with portion of a third exemplary alternative cartridge body (312), using a third exemplary alignment feature (314). As shown in FIGS. 13 and 15, staple drivers (310) include first and second driver members (324, 326) that are connected together using a linking portion (328). First driver portion (324) includes proximal and distal ends (330, 332) that are separated by first and second lateral sides (334, 336). First driver portion (324) includes a staple recess (338) configured to contact a crown (340) of staple (316a) through staple aperture (320a). Second lateral side (336) is disposed opposite to first lateral side (334). First and second lateral sides (334, 136) may extend parallel to and offset from crown (340) of staple (316a). As shown in FIGS. 16A-16B, first driver portion (324) includes an angled contact portion (342) configured to contact a sled (e.g., wedge sled (41)).

Similar to first driver portion (324), second driver portion (326) includes proximal and distal ends (344, 346) that are separated by first and second lateral sides (348, 350). Second driver portion (326) includes a staple recess (352) configured to contact a crown (340) of staple (316b) as staple (316b) moves within and through staple aperture (320a). Second lateral side (350) is disposed opposite to first lateral side (348). First and second lateral sides (348, 350) extend parallel to and offset from crown (340) of staple (316b). Second driver portion (326) includes a slot (354), which is defined by an upper inner wall (356), a lower inner wall (358), and lateral inner walls (360). Lateral inner walls (360) are disposed opposite to upper and lower inner walls (356, 358). Slot (354) may be initially formed with second driver portion (326) or may be subsequently removed from second driver portion (326). For example, slot (354) may be initially formed with second driver portion (326) through an additive manufacturing process (e.g., 3-D printing).

Figure 14:
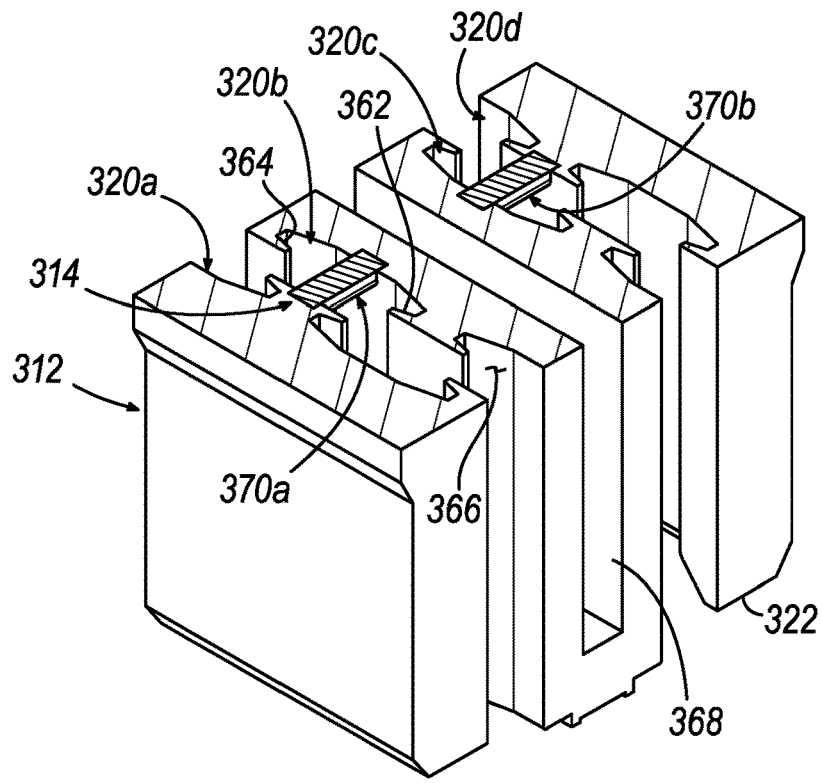
FIG. 14 depicts a partial sectional perspective view of the cartridge body of FIG. 13 including a third exemplary alignment feature.

As shown in FIGS. 13, 14, and 16A-17B, cartridge body (312) includes deck surface (318) and an opposing bottom surface (322). FIG. 14 shows a partial sectional view of cartridge body (312) of FIG. 13. Deck surface (318) extends along a longitudinal axis (LA). Deck surface (318) includes a plurality of staple apertures (320a-d). Each staple aperture (320a-d) includes opposing first and second inner lateral walls (362, 364) that at least partially define an inner surface (366). Cartridge body (312) also includes a knife slot (368). As shown, stapler driver (310a) pushes staple (316a) through staple aperture (320a), stapler driver (310b) pushes staple (316b) through staple aperture (320b), stapler driver (310c) pushes staple (316c) through staple aperture (320c), and staple driver (310d) pushes staple (316d) through staple aperture (320d). In some versions, staple driver (310) and cartridge body (312) may be 3D printed of same material or different materials. In some versions, cartridge body (312) may be formed using additive manufacturing (e.g., 3D printing).

Alignment feature (314) may include at least one alignment member (shown as first and second alignment members (370a-b)) and slot (354). First and second alignment members (370a-b) are configured to extend through at least a portion of staple driver (310) to guide movement of staple driver (310). Alignment members (370a-b) may be coupled with cartridge body (312). As shown in the sectional view of FIG. 14, alignment member (370) may be coupled with cartridge body (312) using a variety of manufacturing processes. For example, alignment members (370a-b) may be coupled with cartridge body (312) using by thermoforming or alignment member with cartridge body (312) or press-fit onto cartridge body (312). In one particular example, alignment members (370a-b) may be in the form of a polymeric pin secured with cartridge body (312) using press-fit or thermal fit. Alignment members (370a-b) may be inserted through slot (354) and then coupled with cartridge body (312). Slots (354) include enclosed vertical slots that allows for a predetermined amount of movement relative to the respective alignment member (370a-b). Slots (354) travel along alignment members (370a-b) so that alignment members (370a-b) retain staple driver (310). The interaction between slot (354) and alignment members (370a-b) maintain staple driver (310) in a vertical orientation. Alignment members (370a-b) may extend laterally through one or more staple apertures (320a-d).

Figure 17A:
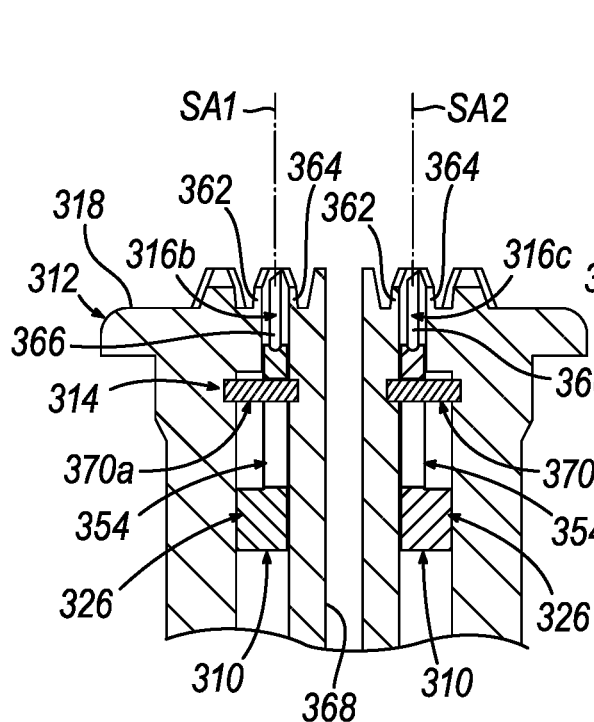
FIG. 17A depicts a sectional view of the cartridge body and the staple driver of FIG. 16A in the non-actuated position.

FIGS. 16A and 17A show a pre-fired state. Particularly, FIG. 16A shows a partial perspective view of cartridge body (312) and staple driver (310) of FIG. 13 in a non-actuated position. FIG. 17A shows a cross-sectional view of staple driver (310) and cartridge body (312) of FIG. 16A. In FIG. 16A, alignment members (370a-b) of cartridge body (312) extend through slot (354) of staple driver (310).

Figure 17B:
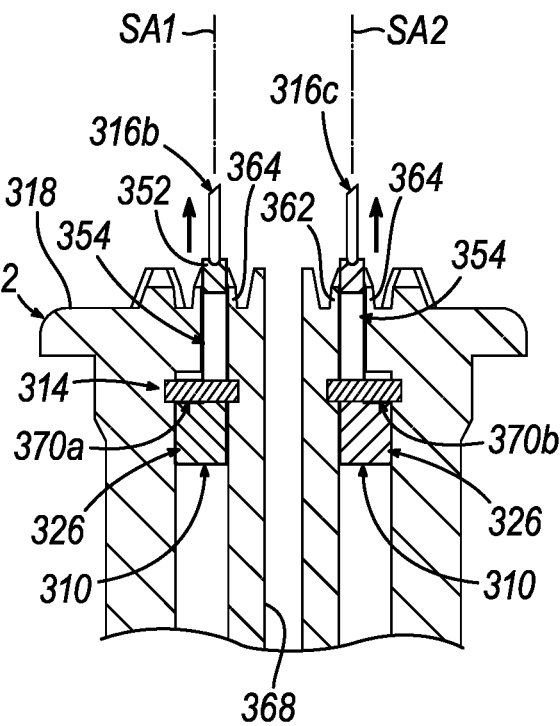
FIG. 17B depicts a sectional view of the cartridge body and the staple driver of FIG. 16B in the actuated position.

FIGS. 16B and 17B show a post-fired state. In moving from the pre-fired state of FIGS. 16A and 17A to the post-fired state of FIGS. 16A and 17A, a wedge sled (372) contacts angled contact portion (342) of staple drivers (310) to push staple drivers (310) toward deck surface (318). FIG. 16B shows a partial perspective view of staple driver (310) and cartridge body (312) of FIG. 16A, but after staple drivers (310) have advanced staples (316b-c) through deck surface (318) of cartridge body (312), and FIG. 17B shows a sectional view of cartridge body (312) and staple driver (310) in actuated position similar to FIG. 16B. As shown in FIGS. 17A-17B, staple apertures (320b-c) define respective staple axes (SA1, SA2). Alignment feature (314) is coupled with cartridge body (312) and extends perpendicular to staple axis (SA1, SA2) of staple apertures (320b-c). Alignment members (370a-b) extend through slots (354) to maintain the orientation of staple drivers (310) as staple drivers (310) move relative to staple apertures (320b-c).

In some versions, a tray (e.g., tray (74)) may be eliminated since slot (354) includes upper inner wall (356) that prevents staple driver (310 from falling out through bottom surface (322) of cartridge body (312). The space previously occupied by the tray may be filled in with staple cartridge material, resulting in thicker walls that enhance the 3D printing (in versions where cartridge body (312) is 3D printed). Additionally, omitting the tray eliminates the lead times associated manufacturing and/or assembly of tray. Regarding staple cartridge (37), proximal and distal walls of staple driver (310) interact with proximal and distal inner walls of staple aperture (51) to maintain staple driver (310) vertically. Alignment members (370a-b) may align staple driver (310) and allow for relaxed tolerances for the length and/or width of staple aperture (320a-d). As a result of the interaction between slot (354) and alignment member (370a-b), tolerances may be held looser for the outline of staple apertures (320a-d) (e.g., tolerances for proximal and distal inner walls of staple aperture (320a-d)).

E. Fourth Exemplary Alternative Staple Drivers, Fourth Exemplary Alternative Cartridge Body, and Fourth Exemplary Alignment Features FIGS. 18-22 show a fourth exemplary alternative staple drivers (410) coupled with a fourth exemplary alternative cartridge body (412) using fourth exemplary alignment features (414). Cartridge body (412) includes a deck surface (418). Deck surface (418) includes a plurality of staple apertures (420). Cartridge body (212) includes a proximal end (424), a distal end (426), a first lateral side (428), and a second lateral side (430) disposed opposite to first lateral side (428). Cartridge body (412) also includes a knife slot (432) that extends along a longitudinal axis (LA) and a bottom surface (434) disposed opposite deck surface (418).

Figure 18:
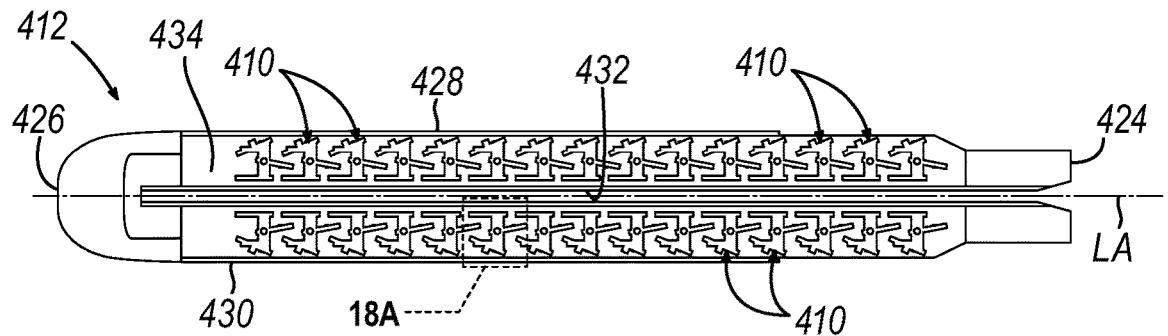
FIG. 18 depicts a bottom view of a fourth exemplary alternative cartridge body coupled with fourth exemplary alternative staple drivers using fourth exemplary alignment features.
Figure 18A:
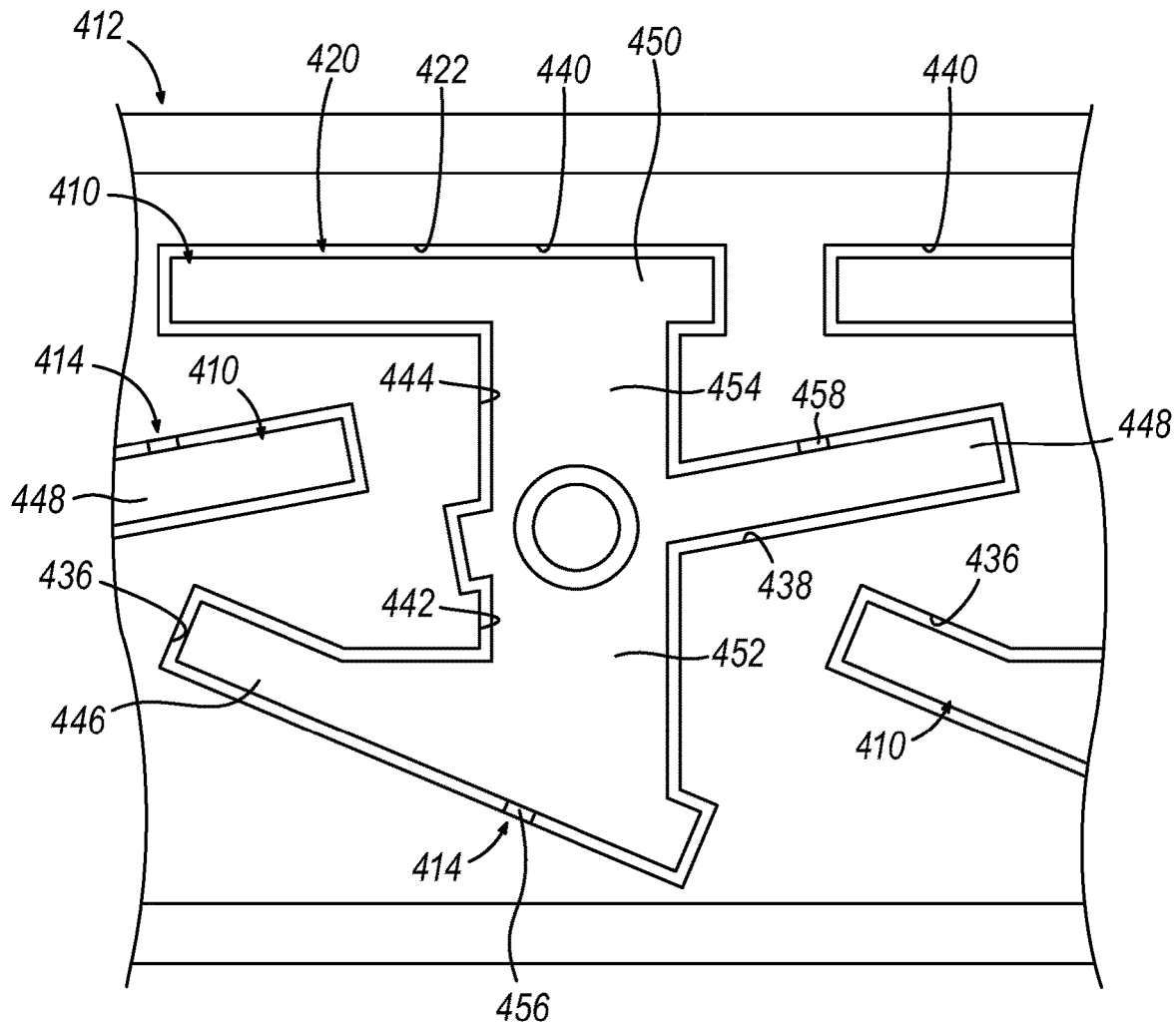
FIG. 18A depicts an enlarged bottom view of the cartridge body and the staple drivers of FIG. 18.

As shown in FIGS. 18A and 19, plurality of staple apertures (420) includes first, second, and third connected staple aperture portions (436, 438, 440) that are connected together using first and second aperture linking portions (442, 444). Particularly, FIG. 18A shows an enlarged bottom view of cartridge body (412) and staple drivers (410) of FIG. 18 and FIG. 19 shows a perspective view of staple drivers (410) and cartridge body (412) of FIG. 18. First connected staple aperture portion (436) extends at a non-zero angle relative to second, and third connected staple aperture portions (438, 440). Similarly, staple driver (410) includes first, second, and third driver portions (446, 448, 450) that are connected together using first and second linking portion (452, 454). First, second, and third connected staple aperture portions (436, 438, 440) and/or first, second, and third driver portions (446, 448, 450) being angled relative to longitudinal axis (LA) defined by knife slot (432) of cartridge body (412).

The geometry of first, second, and third connected staple aperture portions (436, 438, 440) and first, second, and third driver portions (446, 448, 450) allow for stapled tissue to stretch laterally. The lateral stretching may be beneficial for stapling lung tissue, which expands and contracts during breathing. The angle of first, second, and third connected staple aperture portions (436, 438, 440) allows for greater tissue stretching. Features associated with an expandable staple pattern for circular staplers are shown and described in U.S. application Ser. No. 17/401,391, entitled "Methods of Forming an Anastomosis between Organs with an Expandable Tissue Pattern," filed on Aug. 13, 2021, the disclosure of which is incorporated by reference herein in its entirety. While cartridge body (412) includes an inner row of non-angled staples (416), and two inner rows of angled staples (416), more or fewer rows of staples (416) are envisioned.

Alignment feature (414) couples individual staple drivers (410) with cartridge body (412). As shown in FIG. 18A, alignment feature (414) includes at least one connecting portion, shown as first and second connecting portions (456, 458). First and second connecting portions (456, 458) rigidly couple staple driver (410) with staple aperture (420) of cartridge body (412) in a connected state. Since first and second connecting portions (456, 458) are breakable, first and second connecting portions (456, 458) may have a reduced cross-sectional area to reduce the shear force needed to sever first and second connecting portions (456, 458). However, more or fewer connecting portions are also envisioned. At least a portion of first and second connecting portions (456, 458) may remain with staple driver (410) to cause interface with staple aperture (420) of cartridge body (412).

FIG. 20A shows a partial perspective view of staple driver (410) and cartridge body (412) of FIG. 18 in a non-actuated position. As shown in FIG. 18A, first connecting portion (456) connects first connected staple aperture portion (436) with first driver portion (446), and second connecting portion (458) connects second connected staple aperture portion (438) with second driver portion (448). As shown, first and second connecting portions (456, 458) may be disposed at different depths. FIGS. 20A-20B show the cross-sections of staple driver (410) and cartridge body (412) using different hatching patterns for visual clarity, it is envisioned that staple driver (410) and cartridge body (412), and first and second connecting portions (456, 458) of alignment member (414) may be integrally formed together as a unitary piece. Staple driver (410) is configured to move within staple aperture (420) of cartridge body (412) in a disconnected state in response to first and second connecting portions (456, 458) being severed to allow for translation of staple driver (410) relative to cartridge body (412). First and second connecting portions (456, 458) may remain coupled with staple driver (410) in the disconnected state. First and second connecting portions (456, 458) serve as breakable bridges between staple drivers (410) with cartridge body (412). First and second connecting portions (456, 458) may be located at strategic locations so that severed staple drivers (410) travel with cartridge body (412). Staple aperture (420) is defined by an inner surface (422) that includes proximal and distal ends.

FIG. 20B shows a partial perspective view of staple driver (410) and cartridge body (412) of FIG. 20A, but after staple driver (410) has advanced staples (416) through deck surface (418) of cartridge body (412). First, second, and third driver portions (446, 448, 450) push respective staples (416) through first, second, and third connected staple aperture portions (436, 438, 440). First and second connecting portions (456, 458) remain coupled with staple driver (410) in the disconnected state to minimize rotation of staple driver (410) as staple driver (410) advances staple (416) through staple aperture (420) and beyond deck surface (418). Particularly, first and second connecting portions (456, 458) function as interference features and guide staple drivers (410) vertically during firing of staples (416) without twisting or rocking in an undesirable way that may impede actuation of staple drivers (410) during firing. First and second connecting portions (456, 458) may maintain fit and alignment between staple drivers (410) and cartridge body (412) as staple drivers (410) are actuated upwardly during firing. First and second connecting portions (456, 458) may prevent undesired twisting/rocking of staple drivers (410) during firing that may impede actuation of staple drivers (410) during firing.

Figure 21:
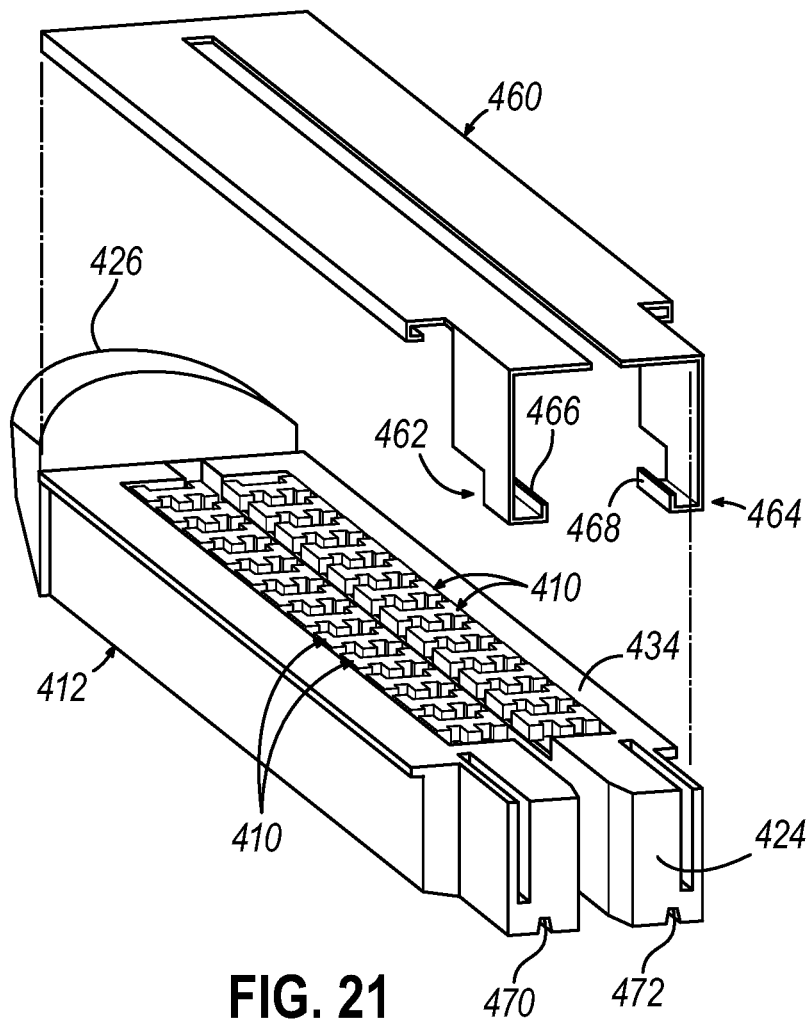
FIG. 21 depicts a perspective view of the cartridge body and staple drivers of FIG. 18 but with a pan shown schematically.
Figure 22:
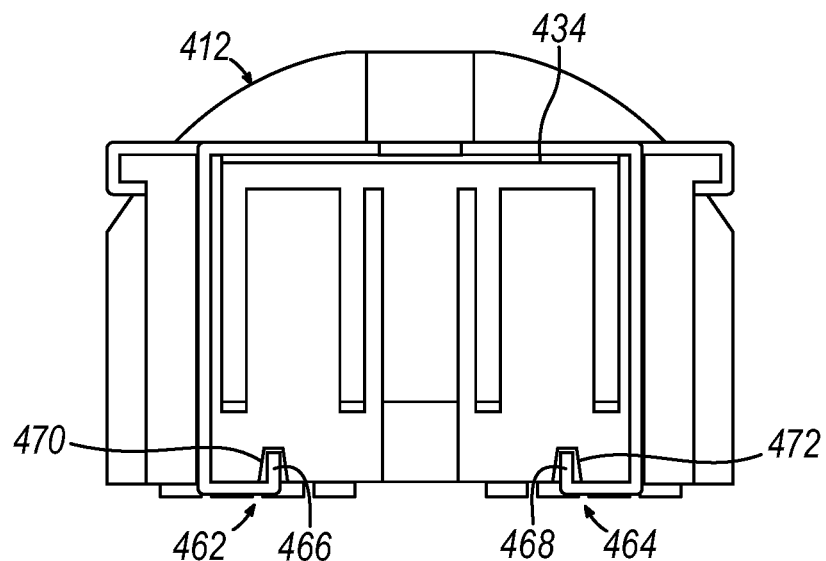
FIG. 22 depicts the cartridge body and the staple drivers of FIG. 18 with the pan coupled with the cartridge body.

FIG. 21 shows a perspective view of cartridge body (412) and staple drivers (410) of FIG. 18 with a tray (460) shown schematically in dashed lines, and FIG. 22 shows cartridge body (412) coupled with tray (460). In some versions, tray may be made of a metallic (e.g., stainless steel) or a polymeric material. As shown, tray (460) includes first and second coupling portions (462, 464). First coupling portion (462) includes a projection (466), and second coupling portion (464) includes a projection (468). Projections (466, 468) may be received by and couple with respective apertures (470, 472) of cartridge body (412). An entirety of cartridge body (412) and staple drivers (410) may be 3D printed using connecting portion (e.g., bridges). In some instances, first, second, and third connected staple aperture portions (436, 438, 440) may be printed simultaneously. By 3D printing staple driver (410) and cartridge body (412) together using alignment features (414), tray (460) may be omitted in some versions that would otherwise be used to retain staple drivers (410) within cartridge body (412). This will also allow a variety of staple drivers (410) to be incorporated without adding additional tooling time and costs. For prototyping, this allows for additional product development flexibility when pursuing multiple versions in parallel that have different geometries.

Figure 23A:
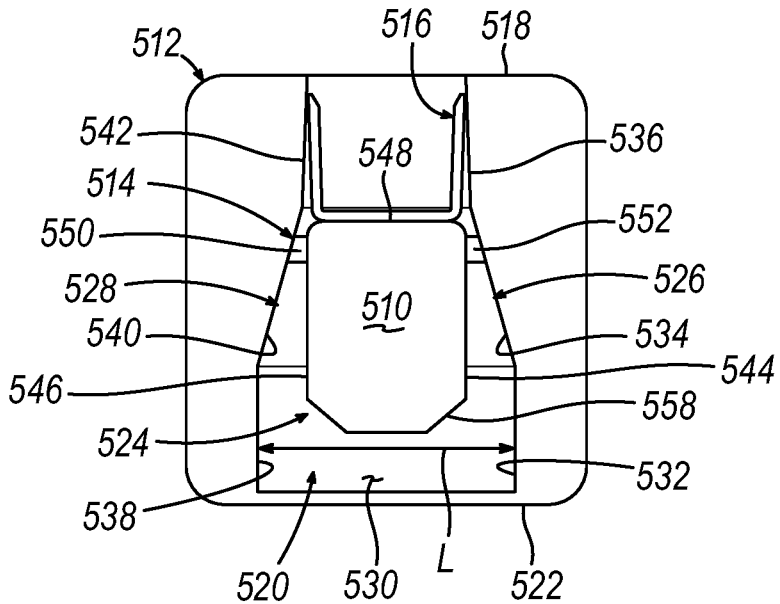
FIG. 23A depicts a schematic sectional view of a fifth exemplary alternative cartridge body coupled with a fifth exemplary alternative staple driver using a fifth exemplary alignment feature in a connected state.
Figure 23B:
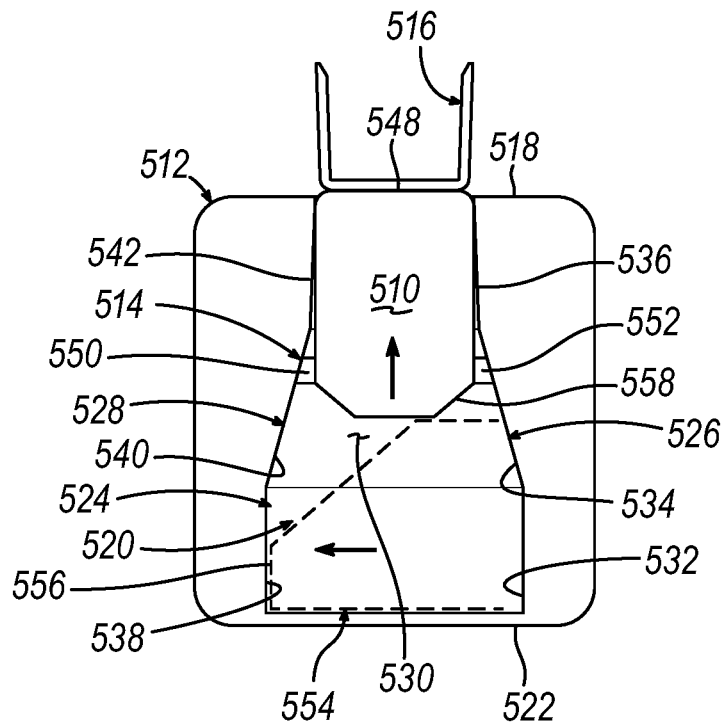
FIG. 23B depicts the cartridge body, the staple driver, and the staple of FIG. 23A but with the staple driver disconnected from the cartridge body and the staple advanced through the staple aperture.

F. Fifth Exemplary Alternative Staple Drivers, Fifth Exemplary Alternative Cartridge Body, and Fifth Exemplary Alignment Feature FIGS. 23A-23B show partial schematic sectional views of a fifth exemplary alternative staple driver (510), a fifth exemplary alternative cartridge body (512), and a fifth exemplary alignment feature (514). Particularly, FIG. 23A shows staple driver (510) and cartridge body (512) coupled together in a connected state, and FIG. 23B shows staple driver (510) disconnected from cartridge body (512) and staple (516) advanced through staple aperture (520). Staple driver (510) and cartridge body (512) may be similar to staple driver (410) and cartridge body (412) described above with reference to FIG. 18-22, except where otherwise described below.

Cartridge body (512) includes a deck surface (518) that is disposed opposite an outer surface (522), which is shown as a bottom surface. Deck surface (518) includes a plurality of staple apertures, with one exemplary staple aperture (520) being shown. Staple aperture (520) is defined by an inner surface (524). Inner surface (524) includes a proximal surface (526), a distal surface (528) that are separated by lateral surfaces (530), with one lateral surface (530) being shown. At least one of proximal or distal surfaces (526, 528) includes a tapered portion configured to slidably receive and guide staple driver (510) toward and subsequently through deck surface (518) in the disconnected state. As shown, proximal surface (526) includes a lower portion (532), an intermediate tapered portion (534), and an upper tapered portion (536). Lower portion (532) is shown as being enclosed. Similarly, distal surface (528) includes a lower portion (538), an intermediate tapered portion (540), and an upper tapered portion (542). While both intermediate tapered portions (534, 540) are both shown to taper inwardly in a similar manner, in some versions only one of intermediate tapered portion (534, 540) may taper inwardly or intermediate tapered portion (534, 540) may taper inwardly to differing magnitudes. Similarly, while both upper tapered portions (536, 542) are shown to taper inwardly in a similar manner. In some versions, only one of upper tapered portions (536, 542) may taper inwardly or upper tapered portions (536, 542) may taper inwardly at differing magnitudes.

Staple driver (510) includes a proximal end (544), a distal end (546), and a staple contact surface (548) disposed therebetween that may contact staple (516). Alignment feature (514) couples staple drivers (510) with cartridge body (512). As shown in FIG. 23A, alignment feature (514) includes at least one connecting portion, shown as first and second connecting portions (550, 552). First and second connecting portions (550, 552) connect inner surface (524) of staple aperture (520) with staple driver (510) in a connected state. First and second connecting portions (550, 552) rigidly couple staple drivers (510) with cartridge body (512). As shown, first and second connecting portions (550, 552) are integrally formed together as a unitary piece together with inner surface (524) of staple aperture (520) and proximal and distal ends (544, 546) of staple driver (510). Particularly, first connecting portion (550) is shown as being formed with intermediate tapered portion (540) of distal surface (528), and second connecting portion (552) is shown as being formed with intermediate tapered portion (534) of proximal surface (526).

Unlike first and second connecting portions (456, 458) that travel together with staple drivers (410) as staple driver (410) move toward and subsequently through deck surface (418), first and second connecting portions (550, 552) are shown as remaining substantially coupled with inner surface (524) of staple aperture (520). However, it is envisioned that a small portion of first and second connecting portions (550, 552) may remain coupled with staple driver (510) as staple driver (510) moves toward and subsequently through deck surface (518) such that first and second connecting portions (550, 552) function as an alignment feature. Staple driver (510) may be guided through staple aperture (520) using first and second connecting portions (550, 552) and/or upper tapered portions (536, 542) of proximal or distal surfaces (526, 528). Upper tapered portions (536, 542) of proximal and distal surfaces (526, 528) cause a progressively tighter fit as staple drivers (510) are lifted by a wedge sled (554), which is shown schematically. As shown in FIG. 23B, an angled surface (556) of wedge sled (554) contacts an angled surface (558) of staple driver to staple driver (510). As a length (L) between proximal or distal surfaces (526, 528) decreases, the distance between proximal and distal ends (544, 546) and proximal or distal surfaces (526, 528) decreases. This decrease in length (L) may decrease the likelihood of staple driver (510) inadvertently rotating within staple aperture (520) which may cause jamming and/or partial deployment of staple (516). While the only coupling between staple driver (510) and cartridge body (512) is at first and second connecting portions (550, 552), additional connecting portions are also envisioned.

The relative positioning of staple driver (510) and cartridge body (512) allow staple driver (510) and cartridge body (512) to be manufactured from the same material, and in some instances, simultaneously. For example, it may be beneficial to perform 3D printing in a single manufacturing step, so that staple drivers (510) do not need to be manually placed. Intermediate tapered portion (534, 540) being inwardly tapering may allow for staple driver (510) and cartridge body (512) and to be printed simultaneously. First and second connecting portions (550, 552) function as break away tabs for 3D printing of staple driver (510) and cartridge body (512) that move relative to one another. The initial positions of staple driver (510) and cartridge body (512) allow printing access to make tapered or wide features that get tighter as staple driver (510) moves within cartridge body (512). Particularly, since there exists a gap between distal end (546) of staple driver (510) and distal surface (528) and between proximal end (544) of staple driver (510) and proximal surface (526), staple driver (510) and cartridge body (512) may be 3D printed simultaneously (e.g., using a single 3D printing process). Without the tapering at least one of proximal or distal surfaces (526, 528), the ribs or walls may limited to no interference as staple driver (510) moves toward and subsequently through deck surface (518) of cartridge body (512).

Figure 24A:
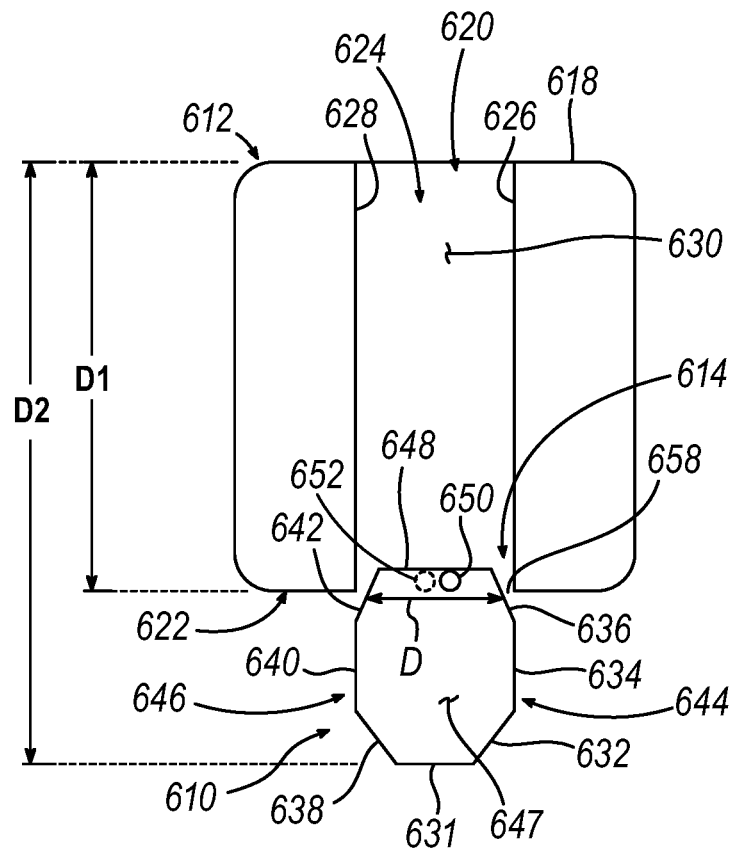
FIG. 24A depicts a schematic sectional view of a sixth exemplary alternative cartridge body coupled with a sixth exemplary alternative staple driver using a sixth exemplary alignment feature where the staple driver is disposed at least partially outside of the cartridge body in a connected state.
Figure 24B:
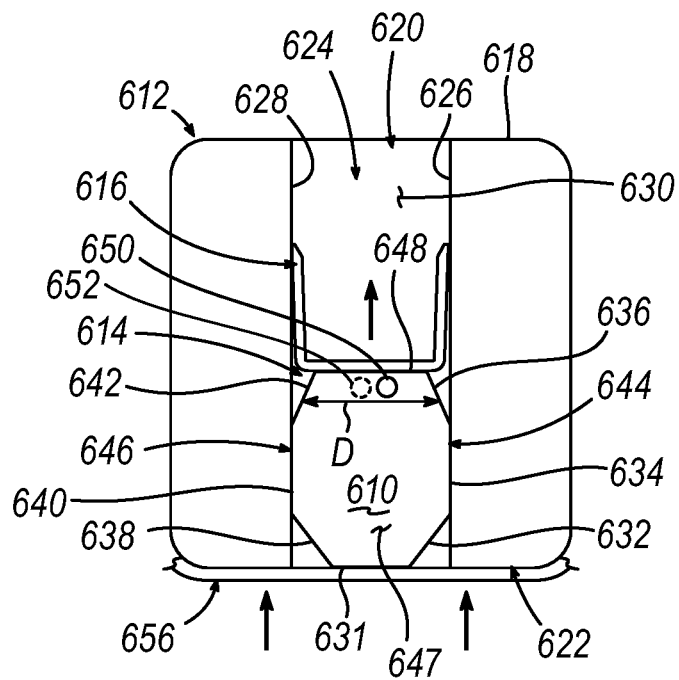
FIG. 24B depicts a schematic sectional view of the cartridge body, the staple driver, and the staple of FIG. 24A but with the staple driver disconnected from the cartridge body and the staple disposed within the staple aperture.

G. Sixth Exemplary Alternative Staple Drivers, Sixth Exemplary Alternative Cartridge Body, and Sixth Exemplary Alignment Features FIGS. 24A-24B show partial schematic sectional views a sixth exemplary alternative staple driver (610), a sixth exemplary alternative cartridge body (612), and a sixth exemplary alignment feature (614). Particularly, FIG. 24A shows staple driver (610) and cartridge body (612) coupled together in a connected state using alignment feature (614), and FIG. 24B shows staple driver (610) disconnected from cartridge body (612) and staple (616) advanced partially through staple aperture (620). Staple driver (610), cartridge body (612), and alignment feature (614) may be similar to staple driver (510), cartridge body (512), and alignment feature (514) described above with reference to FIG. 23A-23B, except where otherwise described below.

Similar to cartridge body (512), cartridge body (612) includes a deck surface (618) which is disposed opposite an outer surface (622). Deck surface (618) includes a plurality of staple apertures, with one exemplary staple aperture (620) being shown. Staple aperture (620) is defined by an inner surface (624). Inner surface (624) includes a proximal surface (626), a distal surface (628), and lateral surfaces (630), with one lateral surface (630) being shown. Outer surface (622) is separated by a first distance (D1) from deck surface (618). In the connected state shown in FIG. 24A, a lower end (631) of staple driver (610) extends at a second distance (D2) from deck surface. Second distance (D2) is greater than first distance (D1). While not shown but similar to inner surface (524), inner surface (624) of staple aperture (620) may include a tapered portion configured to slidably receive and guide staple driver (610) toward and subsequently through deck surface (618) in the disconnected state.

Similar to staple driver (510), staple driver (610) includes a proximal end (644), a distal end (646), a first lateral side (647), a second lateral side (not shown but similar to first lateral side (647)), and a staple contact surface (648). First lateral side (647) and second lateral side (not shown) are disposed between proximal and distal ends (644, 646). Staple contact surface (648) may contact staple (616). As shown, proximal end (644) of staple driver (610) includes a lower tapered portion (632), an intermediate portion (634), and an upper tapered portion (636). Similarly, distal end (646) of staple driver (610) includes a lower tapered portion (638), an intermediate portion (640), and an upper tapered portion (642). Upper tapered portions (636, 642) of staple driver (610) are shown to taper inwardly in a similar manner. In some versions, only one of upper tapered portions (636, 642) may taper inwardly or upper tapered portions (636, 642) may taper inwardly at differing magnitudes. Lower tapered portions (632, 638) may contact a wedge sled (not shown).

Alignment feature (614) includes upper tapered portions (636, 642). Alignment feature (614) may also include at least one connecting portion, shown as first and second connecting portions (650, 652) that connect staple driver (610) and cartridge body (612). As shown in FIG. 24A, first and second connecting portions (650, 652) connect staple aperture (620) with staple driver (610) in the connected state. First and second connecting portions (650, 652) may be similar to first and second connecting portions (456, 458) shown and described with reference to FIGS. 20A-20B. While first and second connecting portions (650, 652) are shown, more or fewer connecting portions (650, 652) are envisioned. First connecting portion (650) may be integrally formed as a unitary piece together with first lateral side (647) of staple driver (610) and a lateral surface (not shown but similar to lateral surface (630)) of inner surface (624). Similarly, second connecting portion (652) may be integrally formed as a unitary piece together with the second lateral side (not shown) of staple driver (610) and lateral surface (630) of inner surface (624). In other words, first and second connecting portions (650, 652) are disposed on opposing lateral sides of staple driver (610). While first and second connecting portions (650, 652) are shown as being offset on opposing lateral sides of staple driver (610), first and second connecting portions (650, 652) may be positioned in the same position on opposing lateral sides. First and second connecting portions (650, 652) rigidly couple staple driver (610) with cartridge body (612).

Similar to first and second connecting portions (456, 458), first and second connecting portions (650, 652) are shown as remaining substantially with lateral surfaces (647) of staple driver (610) as staple driver (610) moves relative to staple aperture (620). However, it is envisioned that a small portion of first and second connecting portions (650, 652) may remain with lateral surface (630) of inner surface (624), as staple driver (610) moves toward and subsequently through deck surface (618) similar to first and second connecting portions (550, 552) remaining with proximal and distal surfaces (526, 528) in FIG. 23B. Staple driver (610) may be guided through staple aperture (620) using first and second connecting portions (650, 652) and/or upper tapered portions (636, 642) of proximal or distal surfaces (626, 628) of staple driver (610). Upper tapered portions (636, 642) of staple driver (610) may align staple driver (610) within staple aperture (620) in moving from the connected state to the disconnected state. For upper tapered portions (636, 642), the distance (D) between proximal and distal ends (644, 646) decreases moving toward staple contacting surface (648). This decrease in distance (D) may minimize the likelihood of staple driver (610) inadvertently rotating within staple aperture (620), which may cause jamming and/or partial deployment of staple (616) in some instances.

The relative positioning of staple driver (610) and cartridge body (612) allow staple driver (610) and cartridge body (612) to be manufactured from the same material, and in some instances, simultaneously. For example, it may be beneficial to perform 3D printing in a single manufacturing step, so that staple drivers (610) are not manually placed. Upper tapered portions (636, 642) being inwardly tapering may allow for staple driver (610) and cartridge body (612) and to be printed simultaneously using first and second connecting portions (650, 652). First and second connecting portions (650, 652) functions as a break away tab for 3D printing of staple driver (610) and cartridge body (612) that move relative to one another. Without the tapering at least one of upper tapered portions (636, 642), the ribs or walls would be limited to no interference as staple driver (610) moves toward and subsequently through deck surface (618) of cartridge body (612). The initial positions of staple driver (610) and cartridge body (612) allow printing access to make tapered features that cause a tighter fit as staple driver (610) moves within cartridge body (612).

As shown in FIG. 24A, staple driver (610) is 3D printed to extend at least partially outside outer wall (622). Staple driver (610) may be 3D printed in a position that is mostly outside cartridge body (612). After printing, staple drivers (610) may be pushed upwardly into staple apertures (620), thereby breaking first and second connecting portions (650, 652). As shown in FIG. 24B, a tray (656) may be optionally inserted to aid in disconnecting staple drivers (610) from cartridge body (612) and/or to prevent staple drivers (610) from falling out through gap (658) (e.g., during transport of packaged staple cartridges).

H. Seventh Exemplary Alternative Staple Drivers, Seventh Exemplary Alternative Cartridge Body, Seventh Exemplary Alignment Features Manual loading of staple drivers (43) into cartridge body (70) of FIG. 6 may be difficult and/or time consuming. For example, it may be challenging to align staple drivers (43) within respective staple apertures (51). Regarding prototyping, inconsistent loading may provide deceased confidence for testing results and analysis.

Figure 25:
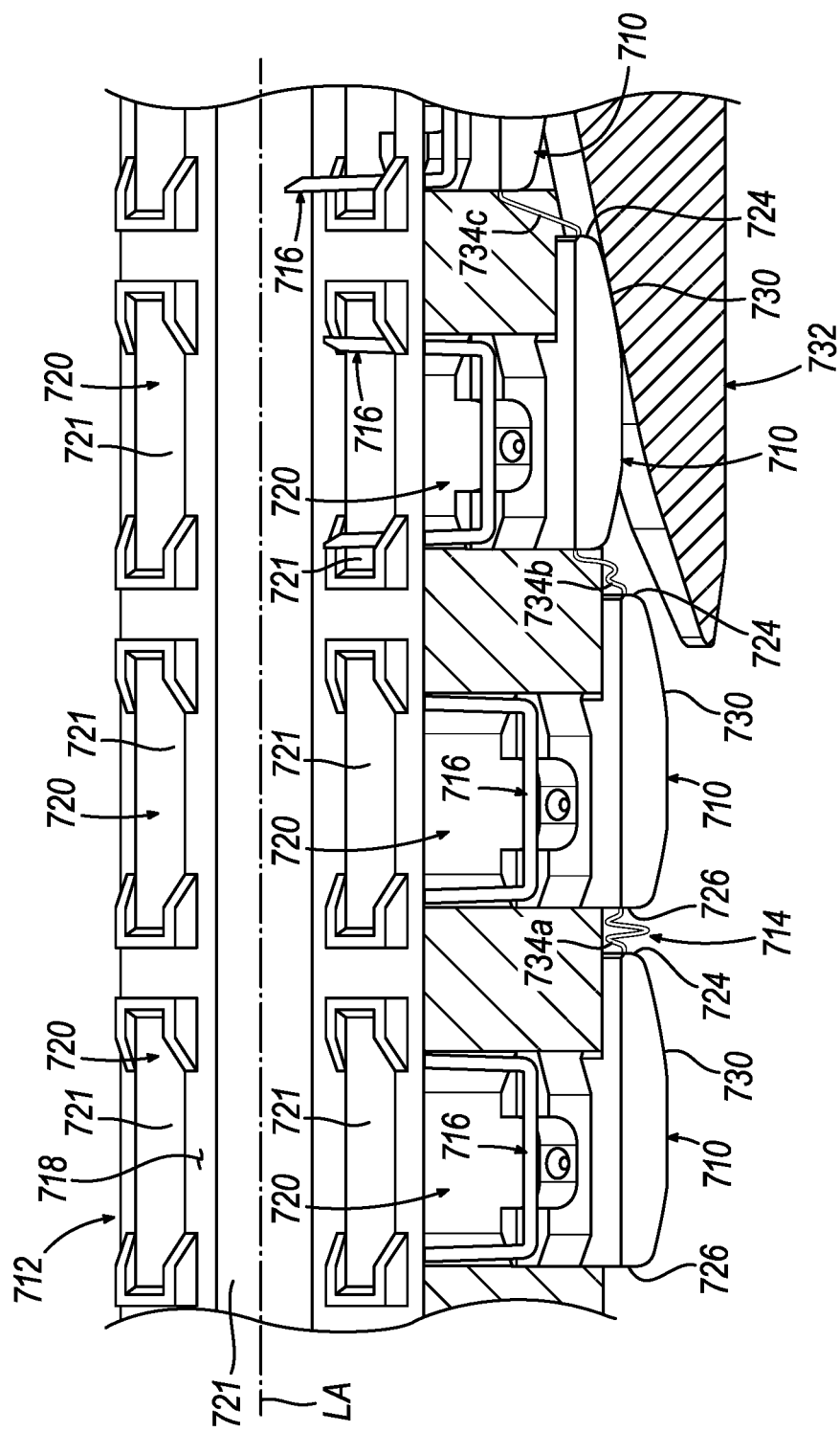
FIG. 25 depicts a perspective view of a seventh exemplary alternative cartridge body and a seventh exemplary alternative staple drivers that are linked together using a seventh exemplary alignment feature.

FIG. 25 shows seventh exemplary alternative staple drivers (710) and a seventh exemplary alternative cartridge body (712) that are linked together using a seventh exemplary alignment feature (714). Cartridge body (712) includes a deck surface (718) that extends along a longitudinal axis (LA). Deck surface (718) includes a plurality of staple apertures (720). Staple apertures (720) are defined by an inner surface (721). Cartridge body (712) also includes a knife slot (722). Each staple driver (710) includes a proximal end (724), a distal end (726), and a staple contact surface (728) disposed therebetween that may contact staple (716). Staple driver (710) includes an angled contact portion (730) configured to contact wedge sled (732), which may be similar to wedge sled (41).

Figure 26:
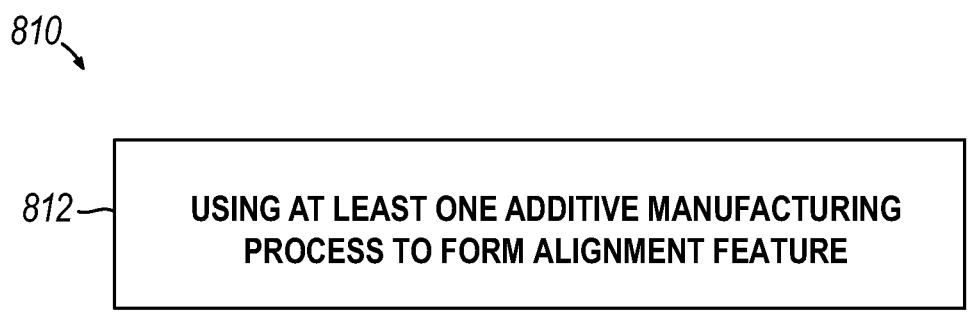
FIG. 26 depicts a diagrammatic view of an exemplary method of manufacture.

Alignment feature (714) is shown as a plurality of flexible connectors (734a-c). As shown, staple drivers (710) are connected in series using flexible connectors (734a-c). Flexible connectors (734a-c) may be formed using a variety of different methods including additive manufacturing (e.g., 3D printing). For example, during 3D printing of staple drivers (710), flexible connectors (734a-c) may be 3D printed in between staple drivers (710) to connect staple drivers (710). Flexible connectors (734a-c) may be printed in a compressed state so as to allow for subsequent extension. FIG. 26 shows the progression of flexible connectors (734a-c) transitioning from the compressed state to the extended state. For example, flexible connector (734a) is shown in a compressed state, flexible connector (734b) is shown in a semi-compressed state, and flexible connector (734c) is shown in a non-compressed state. Staple driver (710) demonstrates the maximum extended link length needed. Flexible connectors (734a-c) orientate staple drivers (710) together making loading of staple drivers (710) within staple apertures (720) easier. The number of connected staple drivers (710) may vary. For example, shorter cartridge bodies (712) may use fewer connected staple drivers (710) than longer cartridge bodies (712). Additionally, multiple assemblies of connected staple drivers (710) may be used for a single staple row. In some versions, five staple drivers (710) may be linked together using four flexible connectors, and in other versions, eight staple drivers (710) may be linked together using seven flexible connectors.

Longitudinally adjacent staple drivers (710) may be connected together with flexible connectors (734a-c) that facilitate loading of staple drivers (710) into cartridge body (712). Flexible connectors (734a-c) may be 3D printed to chain together staple drivers (710), which may be similar a belt hold multiple components together. Flexible connectors (734a-c) allow for use 3D printing allows for quicker prototyping and relatively easier or practically easy to load staple drivers (710) into staple cartridge. Inconsistent loading of staple drivers (710) may lead to difficulties in staples (716) exiting through staple apertures (720), which may cause low confidence for data analysis. Using flexible connectors (734a-c) prevents the user from having to manually place each staple driver (710) individually. Additionally, staple drivers (710) being linked by flexible connectors (734a-c) are retained in the desired position during handling and use.

Flexible connectors (734a-c) may be located adjacent to wedge sled (732), so the flexible connectors (734a-c) do not contact cartridge body (712) during firing. Flexible connectors (734a-c) may sever during firing due to being too short or not being extendable enough. Even if some flexible connectors (734a-c) sever during loading, the unsevered flexible connectors (734a-c) still daisy chain the remaining staple drivers (710) together. Breakage of flexible connectors (734a-c) may occur without affecting the function of staple drivers (710) during loading or during handling or during firing. It is envisioned that some flexible connectors (734a-c) may remain intact after firing and some flexible connectors (734a-c) may sever during firing.

I. Exemplary Method of Manufacturing

A method (810) of manufacturing a portion of a stapling assembly (e.g., a stapling cartridge) is also described with reference to FIG. 26. At step (812), method (810) includes using at least one additive manufacturing process to form alignment feature (114, 214, 314, 414, 514, 614, 714) with at least one of a staple driver (110, 210, 310, 410, 510, 610, 710) or an inner surface (160, 162, 233, 366, 422, 524, 624, 721) of staple aperture (120a-b, 220, 320, 420, 520, 620, 720) that guides the staple driver as staple driver (110, 210, 310, 410, 510, 610, 710) advances staple (116, 216, 316a-c, 416, 516, 616, 716) through staple aperture (120a-b, 220, 320, 420, 520, 620, 720). For example, the additive manufacturing process may include 3D printing.

Using at least one additive manufacturing process to form alignment feature (114, 214, 314, 414, 514, 614, 714) may form at least one of contact feature (122a-h) disposed on a lateral side (134, 136, 148, 150) of staple driver (110), alignment members (370a-b) extending through at least a portion of staple driver (310), connecting portion (456, 458) that rigidly connects staple aperture (520) with the staple driver (510) in a connected state and guides staple driver (510, 610, 710) in the disconnected state, and/or an inwardly tapered portion (534, 536, 540, 542, 636, 642).

In some versions, the at least one additive manufacturing process may form staple driver with a body of stapling assembly (e.g., cartridge body (512, 612, 712) using at least one connecting portion (456, 458, 550, 552, 650, 652). Optionally, method (810) may include severing at least one connecting portion (456, 458, 550, 552, 650, 652) so that staple driver (410, 510, 610) moves relative to inner surface (422, 524, 624) of staple aperture (420, 520, 620).

III. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a staple; (b) a body that includes a deck surface, wherein the deck surface includes a staple aperture, wherein the staple aperture is defined by an inner surface; (c) a staple driver configured to move within the staple aperture; and (d) an alignment feature coupled to or formed with at least one of the staple driver or the inner surface of the staple aperture and configured to minimize rotation of the staple driver as the staple driver advances the staple through the staple aperture of the deck surface, wherein the alignment feature comprises at least one of: (i) a first contact feature projecting beyond a first lateral side of the staple driver and configured to contact the inner surface of the staple aperture as the staple driver advances the staple through the staple aperture, (ii) an alignment member extending through at least a portion of the staple driver and configured to guide movement of the staple driver as the staple driver advances the staple through the staple aperture, (iii) a first connecting portion that rigidly connects the inner surface of the staple aperture with the staple driver in a connected state, wherein in response to the first connecting portion being severed, the first connecting portion is configured to contact and guide the staple driver as the staple driver advances the staple through the staple aperture, or (iv) an inwardly tapering portion of at least one of the inner surface of the staple aperture or the staple driver that is configured to contact the other of the inner surface of the staple aperture or the staple driver and guide the staple driver as the staple driver advances the staple through the staple aperture.

Example 2

The apparatus of Example 1, wherein the alignment feature is formed with at least one of the staple driver or the inner surface of the staple aperture using 3D printing.

Example 3

The apparatus of any one or more of Examples 1 through 2, wherein the alignment feature includes the first contact feature that is configured to slidably contact the inner surface of the staple aperture.

Example 4

The apparatus of Example 3, wherein the first contact feature is formed from a compressible material.

Example 5

The apparatus of any one or more of Examples 3 through 4, wherein the alignment feature further comprises a second contact feature disposed on the first lateral side of the staple driver and configured to slidably contact the inner surface of the staple aperture.

Example 6

The apparatus of any one or more of Example 3 through 4, wherein the staple driver includes a second lateral side disposed opposite to the first lateral side, wherein the alignment feature further comprises a second contact feature disposed on the second lateral side of the staple driver and configured to contact the inner surface of the staple aperture.

Example 7

The apparatus of any one or more of Examples 1 through 6, wherein the staple aperture defines a staple axis, wherein the alignment feature includes the alignment member, wherein the alignment member is coupled with the body and extends perpendicular to the staple axis of the staple aperture.

Example 8

The apparatus of any one or more of Examples 1 through 7, wherein the staple driver includes a slot, wherein the alignment member extends through the slot to maintain an orientation of the staple driver as the staple driver moves relative to the staple aperture.

Example 9

The apparatus of any one or more of Example 1 through 8, wherein the alignment feature includes the first connecting portion, wherein the first connecting portion remains coupled with the staple driver in a disconnected state.

Example 10

The apparatus of any one or more of Examples 1 through 9, wherein the alignment feature includes the first connecting portion, wherein the alignment feature further comprises a second connecting portion that rigidly connects the staple aperture with the staple driver in the connected state, wherein the staple driver is configured to move within the staple aperture of the body in the disconnected state in response to the first and second connecting portions being severed.

Example 11

The apparatus of any one or more of Examples 1 through 10, wherein the alignment feature includes the inwardly tapering portion, wherein the inner surface of the staple aperture includes proximal and distal surfaces, wherein at least one of the proximal or distal surfaces includes the inwardly tapering portion to slidably receive the staple driver in the disconnected state.

Example 12

The apparatus of any one or more of Examples 1 through 11, wherein the alignment feature includes the inwardly tapering portion of the inner surface of the staple aperture, the apparatus further comprising a first connecting portion that rigidly connects the inner surface of the staple aperture with the staple driver in a connected state.

Example 13

The apparatus of any one or more of Examples 1 through 11, wherein the alignment feature includes the inwardly tapering portion of the staple driver, the apparatus further comprising a first connecting portion that rigidly connects the inner surface of the staple aperture with the staple driver in a connected state, wherein the body includes an outer surface disposed opposite to the deck surface and separated by a first distance from the deck surface, wherein in the connected state the staple driver extends at a second distance from the deck surface, wherein the second distance is greater than the first distance.

Example 14

The apparatus of any one or more of Examples 1 through 13, (a) a plurality of staple apertures that includes the staple aperture; and (b) a plurality of staples disposed within the plurality of staple apertures, wherein plurality of staples includes the staple.

Example 15

The apparatus of any one or more of Examples 1 through 14, further comprising: (a) a surgical instrument that includes a staple cartridge receiving portion; and (b) a staple cartridge that includes the staple, the body, the staple driver, and the alignment feature, wherein the staple cartridge is configured to be operatively coupled with the staple cartridge receiving portion.

Example 16

The apparatus of any one or more of Examples 1 through 15, wherein the staple aperture opens to an underside of the body, wherein the apparatus is configured to retain the staple driver within the staple aperture in the absence of a tray coupled with the underside of the bottom.

Example 17

An apparatus comprising: (a) a staple; (b) a body that includes a deck surface, wherein the deck surface includes a staple aperture, wherein the staple aperture defines an inner surface; (c) a staple driver configured to transition relative to the body between a connected state and a disconnected state, wherein the staple driver in the disconnected state is movable within the staple aperture to advance the staple relative to the deck surface; and (d) a first connecting portion that rigidly connects the staple aperture with the staple driver in the connected state, wherein the staple driver is configured to transition from the connected state to the disconnected state in response to the first connecting portion being severed, wherein at least one of: (i) the first connecting portion is configured to remain coupled with the staple driver in the disconnected state to minimize rotation of the staple driver as the staple driver advances the staple through the staple aperture of the deck surface, (ii) the staple driver includes an inwardly tapering portion configured to contact and guide the inner surface of the staple aperture in the disconnected state as the staple driver advances the staple through the staple aperture of the deck surface, or (iii) the inner surface of the staple aperture includes an inwardly tapering portion configured to contact and guide the staple driver in the disconnected state as the staple driver advances the staple through the staple aperture of the deck surface.

Example 18

The apparatus of Example 17, further comprising further comprising a second connecting portion that rigidly connects the staple aperture with the staple driver in the connected state, wherein the staple driver is configured to move together with the first and second connecting portions within the staple aperture of the body in the disconnected state in response to the first and second connecting portions being severed.

Example 19

The apparatus of any one or more of Examples 16 through 18, wherein the inner surface of the staple aperture includes proximal and distal ends, wherein at least one of the proximal or distal ends includes the inwardly tapered portion configured to slidably receive the staple driver.

Example 20

A method of manufacturing a portion of a stapling assembly comprising: using at least one additive manufacturing process to form an alignment feature on at least one of a staple driver or an inner surface of a staple aperture of the stapling assembly that is configured to guide the staple driver as the staple driver advances a staple through the staple aperture, forming the alignment feature further comprising at least one of: (a) forming a contact feature on a lateral side of the staple driver; (b) forming an alignment member to extend through at least a portion of the staple driver; (c) forming a connecting portion that rigidly connects the inner surface of the staple aperture with the staple driver in a connected state; or (d) forming an inwardly tapering portion of at least one of the inner surface of the staple aperture or the staple driver.

Example 21

The method of Example 20, wherein using at least one additive manufacturing process further comprises using at least one additive manufacturing process to form a staple driver in the connected state, the method further comprising severing the connecting portion so that the staple driver moves relative to the inner surface of the staple aperture in the disconnected state.

IV. Miscellaneous

Any one or more of the teachings, expressions, embodiments, examples, etc. described herein may be combined with any one or more of the teachings, expressions, embodiments, examples, etc. described in U.S. patent application Ser. No. 17/951,612, entitled "Surgical Stapler Cartridge with Support Features," filed on Sep. 23, 2022, published as U.S. Pub. No. 2023/030996 on Oct. 5, 2023, the disclosure of which is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a staple;
   (b) a body that includes a deck surface, wherein the deck surface includes a staple aperture, wherein the staple aperture is defined by an inner surface;
   (c) a staple driver configured to move within the staple aperture; and
   (d) a first connecting portion that rigidly connects the inner surface of the staple aperture with the staple driver in a connected state, wherein in response to the first connecting portion being severed, the first connecting portion is configured to guide the staple driver as the staple driver advances the staple through the staple aperture.

2. The apparatus of claim 1, wherein the first connecting portion remains coupled with the staple driver in a disconnected state.

3. The apparatus of claim 1, further comprising a second connecting portion that rigidly connects the staple aperture with the staple driver in the connected state, wherein the staple driver is configured to move within the staple aperture of the body in a disconnected state in response to the first and second connecting portions being severed.

4. The apparatus of claim 1, further comprising:
   (a) a plurality of staple apertures that includes the staple aperture; and
   (b) a plurality of staples disposed within the plurality of staple apertures, wherein plurality of staples includes the staple.

5. The apparatus of claim 1, further comprising:
   (a) a surgical instrument that includes a staple cartridge receiving portion; and (b) a staple cartridge that includes the staple, the body, and the staple driver, wherein the staple cartridge is configured to be operatively coupled with the staple cartridge receiving portion.

6. The apparatus of claim 1, further comprising a second connecting portion that rigidly connect the staple aperture with the staple driver in the connected state, wherein the second connecting portion and is disposed opposite the first connecting portion.

7. An apparatus comprising:
(a) a staple;
(b) a body that includes a deck surface, wherein the deck surface includes a staple aperture, wherein the staple aperture defines an inner surface;
(c) a staple driver configured to transition relative to the body between a connected state and a disconnected state, wherein the staple driver in the disconnected state is movable within the staple aperture to advance the staple relative to the deck surface; and
(d) a first connecting portion that rigidly connects the staple aperture with the staple driver in the connected state, wherein the staple driver is configured to transition from the connected state to the disconnected state in response to the first connecting portion being severed, wherein at least one of:
  (i) the first connecting portion is configured to remain coupled with the staple driver in the disconnected state to minimize rotation of the staple driver as the staple driver advances the staple through the staple aperture of the deck surface,
  (ii) the staple driver includes an inwardly tapering portion configured to guide the staple driver along the inner surface of the staple aperture in the disconnected state as the staple driver advances the staple through the staple aperture of the deck surface, or
  (iii) the inner surface of the staple aperture includes an inwardly tapering portion configured to guide the staple driver in the disconnected state as the staple driver advances the staple through the staple aperture of the deck surface.

8. The apparatus of claim 7, wherein the inner surface of the staple aperture includes proximal and distal surfaces, wherein at least one of the proximal or distal surfaces includes the inwardly tapering portion to slidably receive the staple driver in the disconnected state.

9. The apparatus of claim 7, wherein the body includes an outer surface disposed opposite to the deck surface and separated by a first distance from the deck surface, wherein in the connected state the staple driver extends at a second distance from the deck surface, wherein the second distance is greater than the first distance.

10. The apparatus of claim 7, wherein the inner surface of the staple aperture includes proximal and distal ends, wherein at least one of the proximal or distal ends includes the inwardly tapering portion configured to slidably receive the staple driver.

11. A method of manufacturing a portion of a stapling assembly comprising:
(a) using at least one additive manufacturing process to form a connecting portion that rigidly connects an inner surface of a staple aperture with a staple driver in a connected state; and
(b) severing the connecting portion so that the staple driver moves relative to the inner surface of the staple aperture in a disconnected state.

12. The method of claim 11, further comprising guiding the staple driver using the connecting portion as the staple driver advances a staple through the staple aperture.

13. An apparatus comprising:
(a) a staple;
(b) a body that includes a deck surface, wherein the deck surface includes a staple aperture, wherein the staple aperture defines an inner surface;
(c) a staple driver configured to transition relative to the body between a connected state and a disconnected state, wherein the staple driver in the disconnected state is movable within the staple aperture to advance the staple relative to the deck surface; and
(d) first and second connecting portions that rigidly connect the staple aperture with the staple driver in the connected state, wherein the staple driver is configured to transition from the connected state to the disconnected state in response to the first and second connecting portions being severed, wherein at least one of:
  (i) the first connecting portion is configured to remain coupled with the staple driver in the disconnected state to minimize rotation of the staple driver as the staple driver advances the staple through the staple aperture of the deck surface,
  (ii) the staple driver includes an inwardly tapering portion configured to guide the staple driver along the inner surface of the staple aperture in the disconnected state as the staple driver advances the staple through the staple aperture of the deck surface, or
  (iii) the inner surface of the staple aperture includes an inwardly tapering portion configured to guide the staple driver in the disconnected state as the staple driver advances the staple through the staple aperture of the deck surface.

14. The apparatus of claim 13, wherein the second connecting portion is configured to remain coupled with the staple driver in the disconnected state to minimize rotation of the staple driver as the staple driver advances the staple through the staple aperture of the deck surface.

15. The apparatus of claim 13, wherein the second connecting portion is separated a distance from the first connecting portion in the connected state.

16. The apparatus of claim 13, wherein the staple driver is configured to move together with the first and second connecting portions within the staple aperture of the body in the disconnected state in response to the first and second connecting portions being severed.

17. The apparatus of claim 13, wherein the first and second connecting portions have a minimal cross-sectional area configured to minimize a shear force to sever the first and second connecting portions from the staple aperture.

18. The apparatus of claim 13, wherein the staple driver includes first, second, and third driver portions that are connected together using first and second linking portions.

19. The apparatus of claim 13, wherein the first and second connecting portions are disposed on opposing lateral sides of staple driver.

20. The apparatus of claim 13, wherein the inner surface of the staple aperture includes proximal and distal ends, wherein at least one of the proximal or distal ends includes the inwardly tapering portion configured to slidably receive the staple driver.

* * * * *